United States Patent [19]

Ueda et al.

[11] 4,327,093
[45] Apr. 27, 1982

[54] 3,7-DISUBSTITUTED-2 OR 3-CEPHEM-4-CARBOXYLIC ACID COMPOUNDS

[75] Inventors: Ikuo Ueda, Toyonaka; Masakazu Kobayashi; Hisashi Yamada, both of Ikeda; Hiroki Ono, Nagaokakyo, all of Japan

[73] Assignee: Fujisawa Pharmaceutical Co., Ltd., Osaka, Japan

[21] Appl. No.: 85,684

[22] Filed: Oct. 17, 1979

[30] Foreign Application Priority Data

Oct. 24, 1978 [GB] United Kingdom ............... 41754/78

[51] Int. Cl.$^3$ ............................................. C07D 501/38
[52] U.S. Cl. ...................................... 424/246; 544/22; 544/28
[58] Field of Search ....................... 544/27, 16, 22, 26, 544/30

[56] References Cited

U.S. PATENT DOCUMENTS 3,966,717 6/1976 Cook et al. ............................ 544/22
4,011,215 3/1977 Cook et al. ............................ 544/22
4,098,888 7/1978 Ochiai et al. ........................ 544/28

FOREIGN PATENT DOCUMENTS 764160 9/1971 Belgium .
766528 12/1971 Belgium .

*Primary Examiner*—Nicholas S. Rizzo
*Attorney, Agent, or Firm*—Oblon, Fisher, Spivak, McClelland & Maier

[57] ABSTRACT

3,7-Disubstituted-2 or 3-cephem-4-carboxylic acid compounds of the formula:

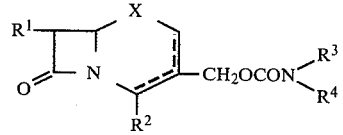

wherein $R^1$ is acylamino or ar(lower)alkylamino; $R^2$ is carboxy or carboxy protected by a pharmaceutically acceptable group; —N—$R^3$, $R^4$ is di(lower)alkylamino(lower)alkylamino, an unsaturated or saturated 3 to 8 membered heteromonocyclic (lower)alkylamino group containing 1 to 4 nitrogen atoms, an unsaturated or saturated 3 to 8 membered heteromonocyclic (lower)alkylamino group containing 1 to 4 nitrogen atoms substituted by lower alkyl or hydroxy(lower) alkyl, an unsaturated or saturated 5 to 6 membered heteromonocyclic group containing 2 to 4 nitrogen atoms, an unsaturated or saturated 5 to 6 membered heteromonocyclic group containing 2 to 4 nitrogen atoms substituted by lower alkyl or hydroxy(lower)alkyl or hydroxypiperidino, and X is —S— or

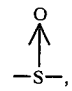

and pharmaceutically acceptable salts thereof. The present compounds are useful for the treatment of infectious diseases in animals and human beings.

9 Claims, No Drawings

3,7-DISUBSTITUTED-2 OR 3-CEPHEM-4-CARBOXYLIC ACID COMPOUNDS

The present invention relates to new 3,7-disubstituted-2 or 3-cephem-4-carboxylic acid compounds and pharmaceutically acceptable salts thereof. More particularly, it relates to new 3,7-disubstituted-2 or 3-cephem-4-carboxylic acid compounds and pharmaceutically acceptable salts thereof which have antibacterial activities and to processes for the preparation thereof, to pharmaceutical composition comprising the same, and to a method of using the same therapeutically in the treatment of infectious diseases in human being and animals.

Accordingly, it is one object of the present invention to provide 3,7-disubstituted-2 or 3-cephem-4-carboxylic acid compounds and pharmaceutically acceptable salts thereof, which are highly active against a number of pathogenic bacteria.

Another object of the present invention is to provide processes for the preparation of 3,7-disubstituted-2 or 3-cephem-4-carboxylic acid compounds and pharmaceutically acceptable salts thereof.

A further object of the present invention is to provide pharmaceutical composition comprising, as active ingredients, said 3,7-disubstituted-2 or 3-cephem-4-carboxylic acid compounds and pharmaceutically acceptable salts thereof.

Still further object of the present invention is to provide a method for the treatment of infectious diseases caused by pathogenic bacteria in human being and animals.

The object 3,7-disubstituted-2 or 3-cephem-4-carboxylic acid compounds are novel and can be represented by the following general formula (I).

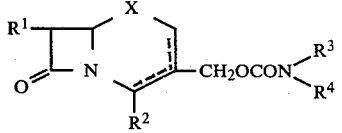

wherein
$R^1$ is amino or a substituted amino group,
$R^2$ is carboxy or a protected carboxy group, the group of the formula:

is a di(lower)alkylamino(lower)alkylamino, a N-containing heterocyclic(lower)alkylamino group which may have suitable substituent(s), a heterocyclic group containing 2 to 4 nitrogen atoms which may have suitable substituent(s) or hydroxypiperidino, and X is —S— or

As to the object compounds (I) and the starting compounds of the present invention, it is to be understood that there may be one or more stereoisomeric pair(s) such as optical and/or geometrical isomers due to asymmetric carbon atom(s) and/or double bond(s) in the molecule, and these isomers are also included within the scope of the present invention. The particulars of such isomers will be made more clear in the following explanation.

According to the present invention, the object compounds (I) can be prepared by following processes which are illustrated by the following schemes.

Process 1

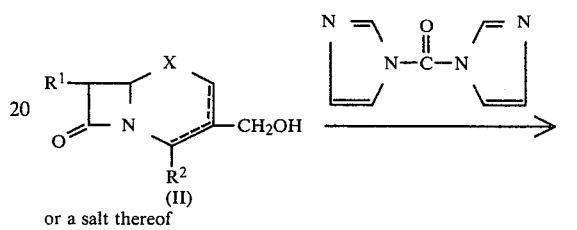

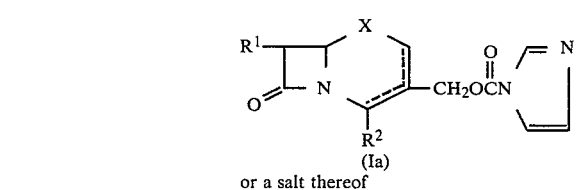

Process 2

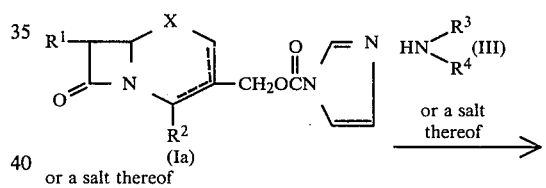

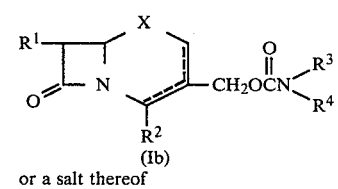

Process 3

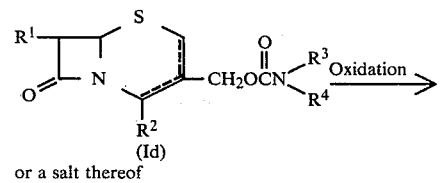

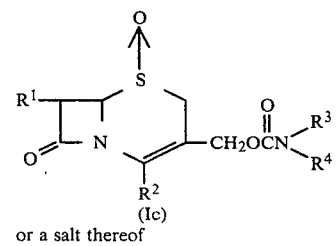

Process 4

-continued

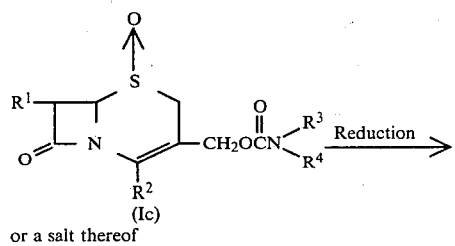
(Ic) or a salt thereof
Reduction →

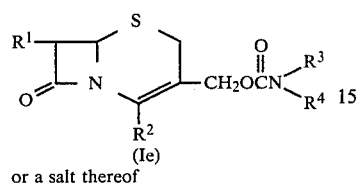
(Ie) or a salt thereof

Process 5

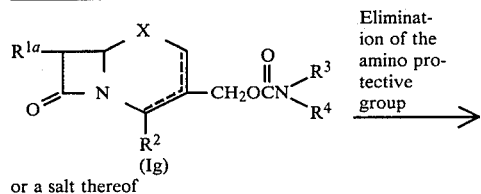
(Ig) or a salt thereof
Elimination of the amino protective group →

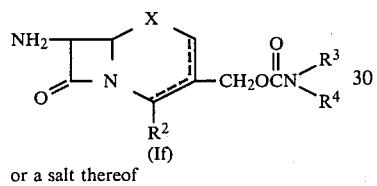
(If) or a salt thereof

Process 6

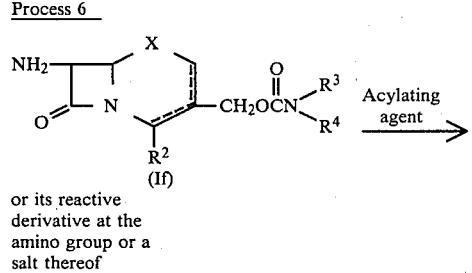
(If) or its reactive derivative at the amino group or a salt thereof
Acylating agent →

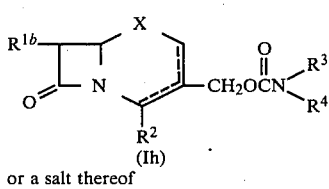
(Ih) or a salt thereof

Process 7

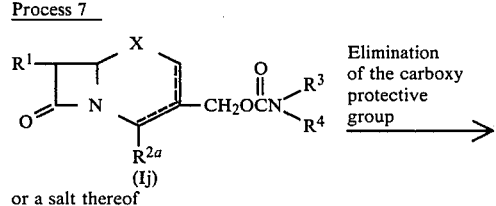
(Ij) or a salt thereof
Elimination of the carboxy protective group →

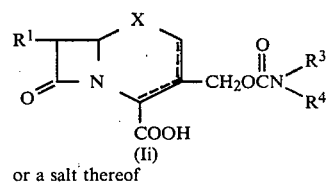
(Ii) or a salt thereof

Process 8

-continued

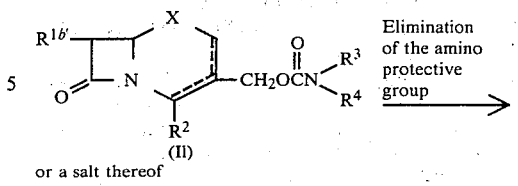
(II) or a salt thereof
Elimination of the amino protective group →

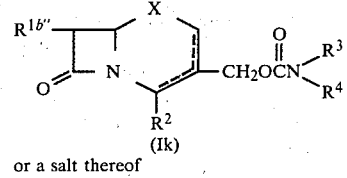
(Ik) or a salt thereof wherein
$R^1$, $R^2$, $R^3$, $R^4$ and X are each as defined above,
$R^{1a}$ is a protected amino group,
$R^{1b}$ is acylamino,
$R^{1b'}$ is acylamino having a protected amino group,
$R^{1b''}$ is acylamino having an amino group, and
$R^{2a}$ is a protected carboxy group.

Suitable pharmaceutically acceptable salts of the object compounds (I) are conventional non-toxic salts and may include a metal salt such as an alkali metal salt (e.g. sodium salt, potassium salt, etc.) and an alkaline earth metal salt (e.g. calcium salt, magnesium salt, etc.), ammonium salt, an organic amine salt (e.g. trimethylamine salt, triethylamine salt, pyridine salt, picoline salt, dicyclohexylamine salt, N,N'-dibenzylethylenediamine salt, etc.), an organic acid salt (e.g. formate, trifluoroacetate, maleate, tartrate, methanesulfonate, benzenesulfonate, toluenesulfonate etc.), an inorganic acid salt (e.g. hydrochloride, hydrobromide, sulfate, phosphate, etc.), or a salt with an amino acid (e.g. arginine, aspartic acid, lysine, glutamic acid, etc.), and the like.

In the above and subsequent description of the present specification, suitable examples and illustrations for the various definitions to be included within the scope of the present invention are explained in details as follows.

The term "lower" is intended to mean 1 to 6 carbon atoms and the term "higher" is intended to mean 7 to 18 carbon atoms, unless otherwise indicated.

Suitable "substituted amino group" may include an amino group substituted by a conventional substituent used in Cephalosporin and Penicillin compounds such as acyl as mentioned below, ar(lower)alkyl (e.g. benzyl, phenethyl, trityl, etc.) or the like.

Suitable "acyl" and "acyl moiety" in the term "acylamino" may include carbamoyl, an aliphatic acyl group, an acyl group containing an aromatic ring (hereinafter referred to as aromatic acyl) and an acyl group containing a heterocyclic ring (hereinafter referred to as heterocyclic acyl).

Suitable example of said acyl may be illustrated as follows:

Aliphatic acyl such as lower or higher alkanoyl (e.g. formyl, acetyl, succinyl, hexanoyl, heptanoyl, stearoyl, etc.);

lower or higher alkoxycarbonyl (e.g. methoxycarbonyl, ethoxycarbonyl, tert-butoxycarbonyl, tert-pentyloxycarbonyl, heptyloxycarbonyl, etc.);

lower or higher alkanesulfonyl (e.g. methanesulfonyl, ethanesulfonyl, etc.); or the like;

Aromatic acyl such as aroyl (e.g. benzoyl, toluoyl, naphthoyl, etc.

ar(lower)alkanoyl (e.g. phenylacetyl, phenylpropionyl, etc.);

aryloxycarbonyl (e.g. phenoxycarbonyl, naphthyloxycarbonyl, etc.);

ar(lower)alkoxycarbonyl (e.g. benzyloxycarbonyl, phenethyloxycarbonyl, etc.);

aryloxy(lower)alkanoyl (e.g. phenoxyacetyl, phenoxypropionyl, etc.);

arylglyoxyloyl (e.g. phenylglyoxyloyl, naphthylglyoxyloyl, etc.);

arenesulfonyl (e.g. benzenesulfonyl, p-toluenesulfonyl, etc.); or the like;

Heterocyclic acyl such as heterocycliccarbonyl (e.g. thenoyl, furoyl, nicotinoyl, etc.);

heterocyclic(lower)alkanoyl (e.g. thienylacetyl, thiazolylacetyl, thiadiazolylacetyl, dithiinylacetyl, pyridylacetyl, pyrimidinylacetyl, triazolylacetyl, tetrazolylacetyl, furylacetyl, oxazolylacetyl, thiazolylpropionyl, etc.);

heterocyclicglyoxyloyl (e.g. thiazolylglyoxyloyl, thienylglyoxyloyl, etc.); or the like.

The acyl and acyl moiety as stated above may have one or more, same or different, suitable substituent(s) such as lower alkyl;

lower alkoxy (e.g. methoxy, ethoxy, propoxy, etc.);

lower alkylthio (e.g. methylthio, ethylthio, etc.);

lower alkylamino (e.g. methylamino, etc.);

halogen (e.g. chlorine, bromine, fluorine or iodine);

amino; a protected amino group as mentioned below; hydroxy; a protected hydroxy such as tetrahydropyranyloxy or acyloxy wherein the acyl moiety is as stated above; imino; oxo;

a group of the formula: =N—OR$^5$ wherein R$^5$ is hydrogen, lower alkyl, lower alkenyl (e.g. vinyl, allyl, 2-butenyl, etc.), lower alkynyl (e.g. ethynyl, 2-propynyl, etc.) or cyclo(lower)alkyl (e.g. cyclopropyl, cyclohexyl, etc.); or the like.

In this connection, when the acyl and acyl moiety have a group of the formula: =N—OR$^5$ (wherein R$^5$ is as defined above) as substituent(s), there are geometrical isomers (syn and anti isomers) due to the presence of double bond. And, for example, the syn isomer means one geometrical isomer having the group of the formula:

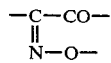

and the corresponding anti isomer means the other geometrical isomer having the group of the formula:

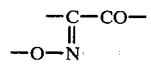

Furthermore, when the heterocyclic moiety in the heterocyclic acyl as stated above is, for example, thiazolyl group having an amino group or a protected amino group, there are tautomeric isomers as shown by the following equilibrium:

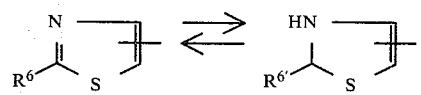

(wherein R$^6$ is amino or a protected amino group and R$^{6'}$ is imino or a protected imino group).

These types of tautomerism between 2-amino-thiazole compounds and 2-iminothiazoline compounds as stated above have been well known in the arts, and it is obvious to a person skilled in the arts that both of the tautomeric isomers are equilibrated and lie in the reciprocally convertible state, and accordingly it is to be understood that such isomers are included within the same category of the compound per se. Accordingly, the both of the tautomeric forms are clearly included within the scope of the present invention. In the present specification, the object and starting compounds including the group of such tautomeric isomers are represented by using one of the expressions therefor, i.e. 2-amino- (or protected amino)thiazolyl and the formula:

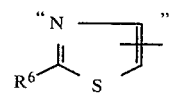

only for the convenient sake.

Preferable example of "substituted amino group" is acylamino, and preferable example of "acylamino" may be illustrated as follows:

Lower alkoxycarbonylamino which may have 1 to 3 halogen atom(s) (e.g. methoxycarbonyl, ethoxycarbonyl, propoxycarbonyl, trichloroethoxycarbonyl, etc.);

Phenyl(lower)alkanoylamino which may have hydroxy and/or amino and/or lower alkoxycarbonylamino group (e.g. phenylacetamido, 2-phenylglycinamido, 2-(4-hydroxyphenyl)glycinamido, N-tert-butoxycarbonyl-2-phenylglycinamido, N-tert-butoxycarbonyl-2-(4-hydroxyphenyl)glycinamido, etc.);

Thiazolyl(lower)alkanoylamino which may have lower alkoxyimino and/or amino and/or lower alkanoylamino [e.g. 2-(2-formamidothiazol-4-yl)acetamido, 2-(2-aminothiazol-4-yl)acetamido, 2-methoxyimino-2-(2-formamidothiazol-4-yl)acetamido, 2-methoxyimino-2-(2-aminothiazol-4-yl)acetamido, 2-ethoxyimino-2-(2-formamidothiazol-4-yl)acetamido, 2-ethoxyimino-2-(2-aminothiazol-4-yl)acetamido, 2-propoxyimino-2-(2-formamidothiazol-4-yl)acetamido, 2-propoxyimino-2-(2-aminothiazol-4-yl)acetamido, 2-isopropoxyimino-2-(2-formamidothiazol-4-yl)acetamido, 2-isopropoxyimino-2-(2-aminothiazol-4-yl)acetamido, etc.];

Thiadiazolyl(lower)alkanoylamino having lower alkoxyimino and/or amino and/or lower alkanoylamino [e.g. 2-methoxyimino-2-(5-formamido-1,2,4-thiadiazol-3-yl)acetamido, 2-methoxyimino-2-(5-amino-1,2,4-thiadiazol-3-yl)acetamido, 2-ethoxyimino-2-(5-formamido-1,2,4-thiadiazol-3-yl)acetamido, 2-ethoxyimino-2-(5-amino-1,2,4-thiadiazol-3-yl)acetamido, etc.];

Furyl(lower)alkanoylamino having lower alkoxyimino [e.g. 2-methoxyimino-2-(2-furyl)acetamido, etc.].

Suitable "protected carboxy group" may include esterified carboxy in which said ester may be those such as lower alkyl ester (e.g. methyl ester, ethyl ester, propyl ester, isopropyl ester, butyl ester, isobutyl ester, tert-butyl ester, pentyl ester, tert-pentyl ester, hexyl ester, 1-cyclopropylethyl ester, etc.);

lower alkenyl ester (e.g. vinyl ester, allyl ester, etc.);

lower alkynyl ester (e.g. ethynyl ester, propynyl ester, etc.);

mono(or di or tri)-halo(lower)alkyl ester (e.g. 2-iodoethyl ester, 2,2,2-trichloroethyl ester, etc.);

lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.); lower alkanesulfonyl(lower)alkyl ester (e.g. 2-mesylethyl ester, etc.); ar(lower)alkyl ester, for example, mono(or di or tri)phenyl(lower)alkyl ester which may have one or more suitable substituent(s) such as lower alkoxy as aforementioned, nitro, hydroxy and lower alkyl as aforementioned (e.g. benzyl ester, 4-methoxybenzyl ester, 4-nitrobenzyl ester, phenethyl ester, benzhydryl ester, bis(methoxyphenyl)methyl ester, 3,4-dimethoxybenzyl ester, 4-hydroxy-3,5-ditertiarybutylbenzyl ester, etc.); aryl ester which may have one or more suitable substituent(s) (e.g. phenyl ester, tolyl ester, tertiarybutylphenyl ester, xylyl ester, mesityl ester, cumenyl ester, etc.), and the like.

Suitable "lower alkyl moiety" in the terms "di(lower)alkylamino(lower)alkylamino" and "N-containing heterocyclic(lower)alkylamino group" may include methyl, ethyl, propyl, isopropyl, butyl, isobutyl, tert-butyl, pentyl, hexyl and the like.

Suitable "N-containing heterocyclic moiety" in the term "N-containing heterocyclic(lower)-alkylamino group which may have suitable substituent(s)" may include unsaturated 3 to 8-membered heteromonocyclic group containing 1 to 4 nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered heteromonocyclic group containing 1 to 4 nitrogen atom(s), for example, pyrrolidinyl, imidazolidinyl, piperidino, piperazinyl, etc.; and the like, wherein said heterocyclic groups may have suitable substituent(s) such as lower alkyl (e.g. methyl, ethyl, propyl, isopropyl, butyl, pentyl, hexyl, etc.), hydroxy(lower)alkyl (e.g. hydroxymethyl, hydroxyethyl, hydroxypropyl, hydroxybutyl, etc.) or the like.

Preferable example of "N-containing heterocyclic (lower)alkylamino group which may have suitable substituent(s)" is lower alkylpyrrolidinyl(lower)alkylamino [e.g. (1-methylpyrrolidin-2-yl)methylamino, (1-ethylpyrrolidin-2-yl)methylamino, 2-(1-ethylpyrrolidin-2-yl)ethylamino, etc.].

Suitable "heterocyclic group containing 2 to 4 nitrogen atoms which may have suitable substituent(s)" may include unsaturated 5 to 6-membered heteromonocyclic group containing 2 to 4 nitrogen atoms, for example, imidazolyl, pyrazolyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), pyrazinyl, pyrimidinyl, pyridazinyl, triazinyl, tetrazinyl, etc.;

saturated 5 to 6-membered heteromonocyclic group containing 2 to 4 nitrogen atoms, for example, imidazolidinyl, pyrazolidinyl, triazolidinyl, tetrazolidinyl, piperazinyl, etc.; and the like, wherein said heterocyclic groups may have suitable substituent(s) such as lower alkyl (e.g. methyl, ethyl, propyl, isopropyl, butyl, pentyl, hexyl, etc.), hydroxy(lower)alkyl (e.g. hydroxymethyl, hydroxyethyl, hydroxypropyl, hydroxybutyl, etc.) or the like.

Preferable example of "heterocyclic group containing 2 to 4 nitrogen atoms which may have suitable substituent(s)" is lower alkylpiperazinyl (e.g. 4-methylpiperazin-1-yl, 4-ethylpiperazin-1-yl, etc.), hydroxy(lower)alkylpiperazinyl [e.g. 4-(2-hydroxyethyl)piperazin-1-yl, etc.] and imidazolyl.

Suitable "protected amino group" may include an amino group substituted by a conventional protective group used in Cephalosporin and Penicillin compounds such as acyl as aforementioned, ar(lower)alkyl as aforementioned, or the like.

The processes for preparing the object compounds (I) of the present invention are explained in details in the following.

PROCESS 1

The object compound (Ia) or a salt thereof can be prepared by reacting the compound (II) or a salt thereof with N,N'-carbonyldiimidazole.

Suitable salts of the compound (II) can be referred to those exemplified for the compound (I).

The present reaction is usually carried out in a solvent such as acetone, dioxane, acetonitril, chloroform, methylene chloride, tetrahydrofuran, ethyl acetate or any other solvents which do not adversely affect the reaction.

The reaction temperature is not critical and the reaction is preferably carried out under cooling or at ambient temperature.

In case that the compound (II) has functional group(s) such as hydroxy, carboxy or amino other than the hydroxymethyl group at 3-position of the cephem ring, the present reaction can preferably be carried out by protecting said functional group(s) with suitable protective group(s) before the present reaction. Further, in case that the compound (II) has a carboxy group, the present reaction can preferably be carried out in the presence of a base as mentioned in Process 5 or by using the compound (II) in the form of the carboxy salt.

The compound (Ia) or a salt thereof produced in the present reaction can also be used in the Process 2 without isolation.

PROCESS 2

The object compound (Ib) or a salt thereof can be prepared by reacting a compound (Ia) or a salt thereof with the compound (III) or a salt thereof.

Suitable salts of the compound (Ia) can be referred to the ones exemplified for the compound (I), and suitable salts of the compound (III) may include an organic acid salt and an inorganic acid salt as exemplified for the compound (I).

The present reaction is usually carried out in a solvent such as water, acetone, dioxane, acetonitrile, chloroform, methylene chloride, ethylene chloride, tetrahydrofuran, ethyl acetate or any other solvents which do not adversely affect the reaction. These solvents may also be used in a mixture with water.

The reaction temperature is not critical and the reaction is preferably carried out under cooling or at ambient temperature.

PROCESS 3

The object compound (Ic) or a salt thereof can be prepared by oxidizing the compound (Id) or salt thereof.

Suitable salts of a compound (Id) can be referred to the ones exemplified for the compound (I).

The present oxidation reaction can be carried out by a conventional method which is applied for the transformation of —S— into

for example by using an oxidizing agent such as m-chloroperbenzoic acid, perbenzoic acid, peracetic acid, ozone, hydrogen peroxide, periodic acid or the like.

The present reaction is usually carried out in a solvent such as water, acetone, dioxane, acetonitril, chloroform, methylene chloride, tetrahydrofuran, ethyl acetate or any other solvents which do not adversely affect the reaction.

The reaction temperature is not critical and the reaction is preferably carried out under cooling or at ambient temperature.

PROCESS 4

The compound (Ie) or a salt thereof can be prepared by reducing the compound (Ic) or a salt thereof.

Suitable salts of the compound (Ic) can be referred to the ones as exemplified for the compound (I).

The present reduction can be carried out by a conventional method which is applied for the transformation of

into —S—, for example, by using phosphorus trichloride, a combination of stannous chloride and acetyl chloride, a combination of an alkali metal iodide (e.g. sodium iodide, etc.) and trihaloacetic anhydride (e.g. trifluoroacetic anhydride, etc.), and the like.

The present reduction is usually carried out in a solvent such as acetone, dioxane, acetonitrile, benzene, hexane, chloroform, methylene chloride, ethylene chloride, tetrahydrofuran, ethyl acetate, or any other solvents which do not adversely affect the reaction.

The reaction temperature is not critical and the reaction is usually carried out under cooling or at ambient temperature.

PROCESS 5

The object compound (If) or a salt thereof can be prepared by subjecting the compound (Ig) or a salt thereof to the elimination reaction of the protective group of the amino.

Suitable salts of the compound (Ig) may include a metal salt, ammonium salt, an organic amine salt and the like as aforementioned.

The present elimination reaction is carried out in accordance with a conventional method such as hydrolysis; reduction; elimination using a Lewis acid; a method by reacting the compound (Ig), wherein the protective group is an acyl group, with an iminohalogenating agent and then with an iminoetherifying agent, and, if necessary, subjecting the resulting compound to hydrolysis; or the like.

The hydrolysis may include a method using an acid or base or hydrazine and the like. These methods may be selected depending on the kind of the protective groups to be eliminated.

Among these methods, hydrolysis using an acid is one of the common and preferable methods for elimination of an acyl group.

Suitable acid may include an organic or an inorganic acid, for example, formic acid, trifluoroacetic acid, benzenesulfonic acid, p-toluenesulfonic acid, hydrochoric acid and the like, and preferable acids are those which can easily be removed from the reaction mixture by a conventional manner such as distillation under reduced pressure, for example, formic acid, trifluoroacetic acid, hydrochloric acid, etc. The acid suitable for the reaction can be selected according to the kind of protective groups to be eliminated. When the elimination reaction is conducted with an acid, it can be carried out in the presence or absence of a solvent. Suitable solvents may include an organic solvent, water or a mixed solvent thereof. When trifluoroacetic acid is used, the elimination reaction may preferably be carried out in the presence of anisole.

The hydrolysis using hydrazine is commonly applied for eliminating the protective groups, for example, succinyl or phthaloyl.

The hydrolysis using a base is preferably applied for elimination of an acyl group. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,5-diazabicyclo[5,4,0]undecene-5 or the like. The hydrolysis using a base is often carried out in water or a hydrophilic organic solvent or a mixed solvent thereof.

Among the protective group, the acyl group can generally be eliminated by hydrolysis as mentioned above or by the other conventional hydrolysis. In case that the acyl group is halo(lower)alkoxycarbonyl or 8-quinolyloxycarbonyl, they are eliminated by treating with a heavy metal such as copper, zinc or the like.

The reductive elimination is generally applied for eliminating the protective group, for example, halo(lower or higher)alkoxycarbonyl (e.g. trichloroethoxycarbonyl, etc.), substituted or unsubstituted ar(lower)alkoxycarbonyl (e.g. benzyloxycarbonyl, etc.), etc. Suitable reduction may include, for example, reduction with an alkali metal borohydride (e.g. sodium borohydride, etc.), reduction using a combination of a metal (e.g. zinc, zinc amalgam, etc.) and an organic or inorganic acid (e.g. acetic acid, propionic acid, hydrochloric acid, etc.), catalytic reduction, and the like.

Suitable iminohalogenating agents used in a method as mentioned above may include phosphorus halide (e.g. phosphorus trichloride, phosphorus pentachloride, phosphorus tribromide, phosphorus pentabromide, etc.), phosphorus oxychloride, thionyl chloride, phosgene and the like. The reaction temperature is not critical, and the reaction is usually carried out at ambient temperature or under cooling. Suitable iminoetherifying agents reacted with thus obtained reaction product may include an alcohol, metal alkoxide and the like. Suitable alcohol may include alkanol (e.g. methanol, ethanol, propanol, isopropanol, butanol, tert-butanol, etc.) which may be substituted wth alkoxy (e.g. methoxy, ethoxy, propoxy, isopropoxy, butoxy, etc.). Suitable metal alkoxide may include alkali metal alkoxide (e.g. sodium alkoxide, potassium alkoxide, etc.), alkaline earth metal alkoxide (e.g. calcium alkoxide, barium alkoxide, etc.) and the like.

The reaction temperature is not critical, and the reaction is usually carried out under cooling at ambient temperature or under warming.

PROCESS 6

The object compound (Ih) or a salt thereof can be prepared by reacting the compound (If) or its reactive derivatives at the amino group or a salt thereof with an acylating agent.

Suitable reactive derivatives at the amino group of the compound (If) may include conventional ones such as Schiff's base type imino or its tautomeric enamine type derivatives formed by the reaction of the compound (If) with a carbonyl compound (e.g. aldehyde, ketone, etc.), isocyanate;

silyl derivatives formed by the reaction of the compound (If) with a silyl compound [e.g. bis(trimethylsilyl)acetamide, trimethylsilylacetamide, etc.];

derivatives formed by the reaction of the compound (If) with phosphorus trichloride or phosgene, or the like.

Suitable salts of the compound (If) can be referred to the ones as exemplified for the compound (I).

The acylating agent to be used for the present reaction may include one of the formulae:

R$^7$—OH  (IV)

wherein R$^7$ is acyl, or its reactive derivatives or a salt thereof.

Suitable acyls can be referred to those exemplified hereinbefore.

Suitable reactive derivatives of the compound (IV) may include an acid halide, an acid anhydride, an activated amide, an activated ester, and the like. The suitable example may be an acid chloride; an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.);

a symmetrical acid anhydride;

an activated amide with imidazole, 4-substituted imidazole, dimethylpyrazole, triazole or tetrazole; an activated ester [e.g. cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesyl-phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)pyridone, N-hydroxysuccinimide, N-hydroxyphthalimide or 1-hydroxy-6-chloro-1H-benzotriazole, and the like.

These reactive derivatives can optionally be selected from them according to the kind of the compound (IV) to be used.

The salts of the compound (IV) may be salt with an inorganic base such as an alkali metal salts (e.g. sodium or potassium salt) or an alkaline earth metal salt (e.g. calcium or magnesium salt), a salt with an organic base such as trimethylamine, triethylamine, dicyclohexylamine or the like.

The present reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. Among these solvents, hydrophilic solvents may be used in a mixture with water.

When the acylating agent is used in a free acid form or its salt form in the reaction, the reaction is preferably carried out in the presence of a conventional condensing agent such as carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N'-carbonylbis(2-mesylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, N-ethylbenzisoxazolium salt, N-ethyl-5-phenyl-isoxazolium-3'-sulfonate, 1-(p-chlorobenzenesulfonyloxy)-6-chloro-1H-benzotriazole, Vilsmeier reagent [e.g. (chloromethylene)dimethylammonium chloride, a compound formed by the reaction of dimethylformamide with phosphorus oxychloride, etc.] or the like.

The reaction may also be carried out in the presence of an inorganic or an organic base such as an alkali metal bicarbonate, alkali metal carbonate, tri(lower)alkylamine, pyridine, di(lower)alkylpyridine, N-(lower)alkylmorphorine, N,N-di(lower)alkylbenzylamine, N,N-di(lower)alkylaniline, or the like. When the base or the condensing agent is in liquid, it can be used also as a solvent. The reaction temperature is not critical, and the reaction is usually carried out under cooling or at ambient temperature.

PROCESS 7

The object compound (Ii) or a salt thereof can be prepared by subjecting the compound (Ij) or a salt thereof to elimination reaction of the protective group of the carboxy.

Suitable salts of the compound (Ij) can be referred to the acid addition salts exemplified for the compound (I).

In the present elimination reaction, all conventional methods used in the elimination reaction of the carboxy protective groups, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid. Suitable base may include an inorganic base and an organic base as aforementioned.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The elimination using Lewis acid is preferable to eliminate substituted or unsubstituted ar(lower)alkyl ester and lower alkyl ester (e.g. tert-butyl ester, 1-cyclopropylethyl ester, etc.), and carried out by reacting the compound (Ij) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide, etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvents which do not adversely affect the reaction. These solvents may be used as a mixture thereof.

The reductive elimination can be applied preferably for elimination of the protective group such as halo(-lower)alkyl ester (e.g. 2-iodoethyl, 2,2,2-trichloroethyl, etc.) or the like. The reduction method applicable for the elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst.

The reaction temperature is not critical, and the reaction is usually carried out under cooling, at ambient temperature or under warming.

PROCESS 8

The object compound (Ik) or a salt thereof can be prepared by subjecting the compound (Il) or a salt thereof to the elimination reaction of the protective group of the amino.

Suitable salts of the compound (Il) can be referred to the ones exemplified for the compound (Ig).

The present elimination reaction is carried out substantially in the same manner as illustrated in Process 5.

The present invention includes, within its scope, the cases that protected amino and/or protected carboxy and/or protected hydroxy group(s) are transformed into the corresponding free amino and/or carboxy and/or hydroxy group(s) according to the reaction conditions and kinds of the protective groups in the course of the aforementioned reactions and/or in post-treatment of the reactions in Processes 1 to 8.

In the aforementioned reactions and/or the post-treating of the reactions in Processes 1 to 8 of the present invention, the aforementioned geometrical isomer and/or tautomeric isomer and/or 2 or 3-cephem isomer may occasionally be transformed into the other geometrical isomer and/or tautomeric isomer and/or 2 or 3-cephem isomer and such cases are to be also included in the scope of the present invention.

In case that the object compound (I) has a free carboxy group and/or a free amino group, it may be transformed into its pharmaceutically acceptable salt as aforementioned by a conventional method.

The object compound (I) of the present invention exhibits high antimicrobial activity and inhibits the growth of a number of microorganisms including pathogenic Gram-positive and Gram-negative bacteria.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention has proved to be effective for treating of infectious diseases caused by a number of pathogenic bacteria. In general amounts, daily dose between 1 mg./body and about 1000 mg/body or even more may be administered.

Now, in order to show the utility of the object compounds (I), test data on anti-microbial activity of a representative compound of the present invention are shown below.

TEST COMPOUND (1) 7-[2-Methoxyimino-2-(2-aminothiazol-4-yl)acetamido]-3-(4-methyl-1-piperazinyl)carbonyloxymethyl-3-cephem-4-carboxylic acid dihydrochloride (syn isomer).

(2) 7-[2-Methoxyimino-2-(5-amino-1,2,4-thiadiazol-3-yl)acetamido]-3-(4-methyl-1-piperazinyl)carbonyloxymethyl-3-cephem-4-carboxylic acid (syn isomer).

One loopful of an overnight culture of each test strain in Trypticase-soy broth ($10^6$ viable cells per ml.) was streaked on heart infusion agar (HI-agar) containing graded concentrations of antibiotics, and the minimal inhibitory concentration (MIC) was expressed in terms of μg/ml after incubation at 37° C. for 20 hours.

| Test results | | |
|---|---|---|
| | MIC (μg/m) | |
| | Test compounds | |
| Test Bacteria | (1) | (2) |
| Klebsiella pneumoniae 20 | 0.10 | 0.05 |
| Proteus mirabilis 18 | 0.05 | 0.20 |

The following examples are given for the purpose of illustrating the present invention.

EXAMPLE 1

A solution of benzhydryl 7-[2-methoxyimino-2-(2-formamidothiazol-4-yl)acetamido]-3-hydroxymethyl-3-cephem-4-carboxylate (syn isomer) (12.15 g) in tetrahydrofuran (240 ml) was stirred under ice-cooling and thereto was added N,N'-carbonyldiimidazole (4.9 g) followed by stirring for an hour at 5° C. The reaction mixture was concentrated to one third volume and to the residue was added ethyl acetate (300 ml). The organic layer was separated therefrom, washed with diluted hydrochloric acid and a saturated aqueous solution of sodium chloride in turn, dried over magnesium sulfate, treated with activated charcoal and then evaporated to give benzhydryl 7-[2-methoxyimino-2-(2-formamidothiazol-4-yl)acetamido]-3-(1-imidazolyl)carbonyloxymethyl-3-cephem-4-carboxylate (syn isomer) (14.0 g).

I.R. (Nujol) 3700-2400, 1770, 1760, 1720, 1660, 1535, 1485, 1450, 1390, 1370, 1310, 1280, 1230, 1160, 1090, 1060, 1030, 995 cm$^{-1}$.

N.M.R. (DMSO-$d_6$, $\delta$) 3.5-4.2 (2H, broad), 3.93 (3H, s), 4.83-5.5 (2H, broad), 5.27 (1H, d, J=4 Hz), 6.0 (1H, d,d, J=4 and 8 Hz), 6.97 (1H, s), 7.1 (2H, s), 7.17-7.67 (10H, m), 8.23 (1H, s), 8.53 (1H, s), 9.77 (1H, d, J=8 Hz), 12.7 (1H, broad).

EXAMPLE 2

To a solution of benzhydryl 7-(2,2,2-trichloroethoxycarboxamido)-3-hydroxymethyl-3-cephem-4-carboxylate (20 g) in tetrahydrofuran (400 ml) was added N,N'-carbonyldiimidazole (6.8 g) with stirring under ice-cooling followed by stirring for 2 hours at 5° C. The reaction mixture was evaporated to one third volume and thereto were added water and ethyl acetate. The ethyl acetate layer was separated therefrom, washed with a saturated aqueous solution of sodium chloride, a diluted hydrochloric acid saturated with sodium chloride and a saturated aqueous solution of sodium chloride in turn and then evaporated. To the residue was added diethyl ether followed by evaporation. The resulting residue was pulverized in diisopropyl ether, collected by filtration and then dried to give a mixture (23 g) of Benzhydryl 7-(2,2,2-trichloroethoxycarboxamido)-3-(1-imidazolyl)carbonyloxymethyl-2-cephem-4-carboxylate and benzhydryl 7-(2,2,2-trichloroethoxycarboxamido)-3-(1-imidazolyl)carbonyloxymethyl-3-cephem-4-carboxylate.

I.R. (Nujol) 3600-3450, 3400-3100, 1800-1700, 1550-1500 cm$^{-1}$

N.M.R. (DMSO-$d_6$, $\delta$) 3.5-4.2 (2H, broad), 4.93 (2H, s), 5.06 (1H, s), 5.62 (1H, s), 4.7-6.0 (4H, m), 6.92 (1H, s), 7.1 (2H, s), 7.23-7.83 (10H, m), 8.2 (1H, s), 9.07 (1H, d, J=8 Hz).

EXAMPLE 3

To a solution of benzhydryl 7-phenylacetamido-3-hydroxymethyl-2-cephem-4-carboxylate (1 g) in dry tetrahydrofuran (20 ml) was added N,N'-carbonyldiimidazole (350 mg) with stirring at room temperature, followed by stirring for 30 minutes at the same temperature. To the reaction mixture were added chloroform and water. The chloroform layer was separated therefrom, washed with water, an aqueous solution of sodium chloride, dried over magnesium sulfate and then evaporated under reduced pressure. The residual oil was pulverized in hexane, collected by filtration and then dried to give benzhydryl 7-phenylacetamido-3-(1-imidazolyl)carbonyloxymethyl-2-cephem-4-carboxylate (1.05 g).

I.R. (Nujol) 3330, 3130, 3060, 3030, 1775, 1760, 1740, 1650, 1530, 1500 cm$^{-1}$.

N.M.R. (DMSO-$d_6$, $\delta$) 3.62 (2H, s), 5.05 (2H, s), 5.16 (1H, d, J=4 Hz), 5.46 (1H, d,d, J=4 and 6 Hz), 5.63 (1H, s), 6.90 (1H, s,), 7.08 (2H, d,d, J=1.5 and 3 Hz), 7.23-7.66 (16H, m), 8.2 (1H, s), 9.23 (1H, d, J=6 Hz).

EXAMPLE 4

The following compounds were obtained according to the similar manners to those in Examples 1-3.

(1) Benzhydryl 7-[2-methoxyimino-2-(2-formamidothiazol-4-yl)acetamido]-3-(1-imidazolyl)carbonyloxymethyl-3-cephem-4-carboxylate-1-oxide (syn isomer).

I.R. (Nujol) 3700-3300, 1790, 1760, 1720, 1680, 1660, 1520 cm$^{-1}$.

(2) Benzhydryl 7-(2,2,2-trichloroethoxycarboxamide)-3-(1-imidazolyl)carbonyloxymethyl-3-cephem-4-carboxylate-1-oxide.

I.R. (Nujol) 3500-3100, 1790, 1760-1700, 1520 cm$^{-1}$.

(3) Benzhydryl 7-phenylacetamido-3-(1-imidazolyl)-carbonyloxymethyl-3-cephem-4-carboxylate-1-oxide.

I.R. (Nujol) 3300, 3600-3100, 1790, 1765, 1710, 1645 cm$^{-1}$.

EXAMPLE 5

To a solution of benzhydryl 7-[2-methoxyimino-2-(2-formamidothiazol-4-yl)acetamido]-3-(1-imidazolyl)carbonyloxymethyl-3-cephem-4-carboxylate (syn isomer)(13.5 g) in tetrahydrofuran (200 ml) was added m-chloroperbenzoic acid (5.8 g) with stirring under ice-cooling, followed by stirring for an hour at 5° C. The reaction mixture was evaporated and the residue was pulverized in diethyl ether, collected by filtration, washed with ethyl acetate and diethyl ether and then dried to give benzhydryl 7-[2-methoxyimino-2-(2-formamidothiazol-4-yl)acetamido]-3-(1-imidazolyl)carbonyloxymethyl-3-cephem-4-carboxylate-1-oxide (syn isomer)(11.0 g).

I.R. (Nujol) 3700-3000, 1790, 1760, 1720, 1680, 1660, 1520 cm$^{-1}$.

N.M.R. (DMSO-$d_6$, $\delta$) 3.5-4.2 (2H, broad), 3.93 (3H, s), 5.03, 5.57 (2H, d,d, J=12 Hz), 5.1 (1H, d, J=4 Hz), 6.13 (1H, d,d, J=4 and 8 Hz), 7.0 (1H, s), 7.1 (2H, s), 7.17-7.83 (10H, m), 8.27 (1H, s), 8.57 (1H, s), 9.2 (1H, d, J=8 Hz).

EXAMPLE 6

To a solution of a mixture of benzhydryl 7-(2,2,2-trichloroethoxycarboxamido)-3-(1-imidazolyl)carbonyloxymethyl-2-cephem-4-carboxylate and benzhydryl 7-(2,2,2-trichloroethoxycarboxamido)-3-(1-imidazolyl)carbonyloxymethyl-3-cephem-4-carboxylate (20 g) in tetrahydrofuran (300 ml) was added m-chloroperbenzoic acid (12.2 g) with stirring under ice-cooling followed by stirring for an hour. The reaction mixture was evaporated and to the residue was added diethyl ether followed by evaporation. The residue was suspended in diethyl ether. The diethyl ether layer was decanted and the residual oil was pulverized in diisopropyl ether, collected by filtration, washed with diisopropyl ether and then dried to give benzhydryl 7-(2,2,2-trichloroethoxycarboxamido)-3-(1-imidazolyl)carbonyloxymethyl-3-cephem-4-carboxylate-1-oxide (16.1 g). The decanted diethyl ether layer and the diisopropyl ether mother liquor were combined together and the precipitates were collected by filtration, washed with diethyl ether and diisopropyl ether and then dried to give the same object compound (4.1 g). Total yield: 20.2 g.

I.R. (Nujol) 3500–3100, 1790, 1760–1700, 1520 cm$^{-1}$.

N.M.R. (DMSO-d$_6$, δ) 3.88, 4.33 (2H, d,d, J=18 Hz), 4.97 (2H, s), 5.15 (1H, d, J=4 Hz), 5.0–5.6 (2H, m), 5.95 (1H, d,d, J=4 and 8 Hz), 7.03 (1H, s), 7.15 (1H, s), 7.3 (1H, s), 7.23–8.0 (10H, m), 8.3 (1H, s), 8.83 (1H, broad s).

EXAMPLE 7

The following compounds were prepared according to the similar manners to those in Examples 5–6.

(1) Benzhydryl 7-(2-phenylacetamido)-3-(1-imidazolyl)carbonyloxymethyl-3-cephem-4-carboxylate-1-oxide.

I.R. (Nujol) 3300, 3600–3100, 1790, 1765, 1710, 1645 cm$^{-1}$.

N.M.R. (DMSO-d$_6$, δ) 3.7 (2H, s), 3.8, 4.27 (2H, d,d, J=16 Hz), 5.05, 5.57 (2H, d,d, J=14 Hz), 4.97 (1H, d, J=4 Hz), 6.02 (1H, d,d, J=4 and 8 Hz), 7.03 (1H, s), 7.13 (2H, s), 7.23–7.83 (10H, m), 8.27 (1H, s), 8.47 (1H, d, J=8 Hz).

(2) Benzhydryl 7-[2-methoxyimino-2-(2-formamidothiazol-4-yl)acetamido]-3-(4-methyl-1-piperazinyl)carbonyloxymethyl-3-cephem-4-carboxylate-1-oxide (syn isomer). This compound was identified with the compound obtained in Example 8 by N.M.R.

(3) Benzhydryl 7-(2,2,2-trichloroethoxycarboxamido-3-(4-methyl-1-piperazinyl)carbonyloxymethyl-3-cephem-4-carboxylate-1-oxide.

I.R. (Nujol) 3700–3100, 1790, 1760–1660, 1640, 1560–1500 cm$^{-1}$.

(4) Benzhydryl 7-phenylacetamido-3-[N-{2-(N,N-dimethylamino)ethyl}carbamoyloxymethyl]-3-cephem-4-carboxylate-1-oxide.

I.R. (Nujol) 3320, 3300, 1790, 1710, 1695, 1645 cm$^{-1}$.

(5) Benzhydryl 7-phenylacetamido-3-(4-methyl-1-piperazinyl)carbonyloxymethyl-3-cephem-4-carboxylate-1-oxide.

I.R. (Nujol) 3300, 1790, 1785, 1720, 1700, 1655 cm$^{-1}$.

(6) Benzhydryl 7-phenylacetamido-3-[4-(2-hydroxyethyl)-1-piperazinyl]carbonyloxymethyl-3-cephem-4-carboxylate-1-oxide.

I.R. (Nujol) 3600–3100, 1785, 1720, 1690, 1650 cm$^{-1}$.

(7) Benzhydryl 7-phenylacetamido-3-(4-hydroxypiperidino)carbonyloxymethyl-3-cephem-4-carboxylate-1-oxide.

I.R. (Nujol) 3700–3100, 1780, 1720, 1700–1670, 1650 cm$^{-1}$.

(8) Benzhydryl 7-phenylacetamido-3-[N-{(1-ethyl-2-pyrrolidinyl)methyl}carbamoyloxymethyl]-3-cephem-4-carboxylate-1-oxide.

I.R. (Nujol) 3300, 1790, 1740–1660, 1690, 1645 cm$^{-1}$.

(9) Benzhydryl 7-amino-3-(4-methyl-1-piperazinyl)-carbonyloxymethyl-3-cephem-4-carboxylate-1-oxide.

I.R. (Nujol) 3700–3100, 1720, 1700, 1640 cm$^{-1}$.

(10) Benzhydryl 7-[2-methoxyimino-2-(5-amino-1,2,4-thiadiazol-3-yl)acetamido]-3-(4-methyl-1-piperazinyl)carbonyloxymethyl-3-cephem-4-carboxylate-1-oxide. (syn isomer).

I.R. (Nujol) 3350, 1790, 1690, 1620, 1460 cm$^{-1}$.

(11) Benzhydryl 7-[2-(2-formamidothiazol-4-yl)acetamido]-3-(4-methyl-1-piperazinyl)carbonyloxymethyl-3-cephem-4-carboxylate-1-oxide.

I.R. (Nujol) 3400, 3300, 1775, 1680, 1530 cm$^{-1}$.

(12) Benzhydryl 7-[D-N-tert-butoxycarbonyl-2-(4-hydroxyphenyl)glycinamido]-3-(4-methyl-1-piperazinyl)carbonyloxymethyl-3-cephem-4-carboxylate-1-oxide.

I.R. (Nujol) 3350, 1790, 1700, 1680, 1610, 1500 cm$^{-1}$.

(13) Benzhydryl 7-[2-propoxyimino-2-(2-formamidothiazol-4-yl)acetamido]-3-(4-methyl-1-piperazinyl)carbonyloxymethyl-3-cephem-4-carboxylate-1-oxide. (syn isomer).

I.R. (Nujol) 3250, 1790, 1700, 1550, 1470 cm$^{-1}$.

(14) Benzhydryl 7-[2-methoxyimino-2-(2-furyl)acetamido]-3-(4-methyl-1-piperazinyl)carbonyloxymethyl-3-cephem-4-carboxylate-1-oxide (syn isomer).

I.R. (Nujol) 1790, 1680, 1520 cm$^{-1}$.

(15) Benzhydryl 7-(D-N-tert-butoxycarbonyl-2-phenylglycinamido)-3-(4-methyl-1-piperazinyl)carbonyloxymethyl-3-cephem-4-carboxylate-1-oxide.

I.R. (Nujol) 3300, 1785, 1685, 1490 cm$^{-1}$.

EXAMPLE 8

To a solution of benzhydryl 7-[2-methoxyimino-2-(2-formamidothiazol-4-yl)acetamido]-3-(1-imidazolyl)carbonyloxymethyl-3-cephem-4-carboxylate-1-oxide (syn isomer)(3.59 g) in a mixture of water (10 ml) and tetrahydrofuran (50 ml) was added 1-methylpiperazine (1.5 g) followed by stirring for 2 hours under ice-cooling. To the reaction mixture was added a mixture of ethyl acetate and water, and the ethyl acetate layer was separated, washed with an aqueous solution of sodium chloride, dried over magnesium sulfate, treated with activated charcoal and then evaporated. The residue was pulverized in ethyl acetate, collected by filtration and then dried to give benzhydryl 7-[2-methoxyimino-2-(2-formamidothiazol-4-yl)acetamido]-3-(4-methyl-1-piperazinyl)carbonyloxymethyl-3-cephem-4-carboxylate-1-oxide (syn isomer)(1.95 g).

N.M.R. (DMSO-d$_6$, δ) 2.2 (3H, s), 2.0–2.5 (4H, m), 3.17–3.67 (4H, m), 3.5–4.33 (2H, broad), 3.97 (3H, s), 4,63, 5.18 (2H, d,d, J=14 Hz), 5.1 (1H, d, J=4 Hz), 6.07 (1H, d,d, J=4 and 8 Hz), 7.0 (1H, s), 7.1–7.7 (10H, m), 8.53 (1H, s), 9.07 (1H, d, J=8 Hz).

EXAMPLE 9

To a solution of benzhydryl 7-phenylacetamido-3-(1-imidazolyl) carbonyloxymethyl-2-cephem-4-carboxylate (300 mg) in a mixture of tetrahydrofuran (5 ml) and water (1 ml) was added 2-(N,N-dimethylamino)ethylamine (44 mg) followed by stirring for an hour at room temperature. The reaction mixture was evaporated and to the residue were added water and ethyl acetate. The ethyl acetate layer was separated and the remaining aqueous layer was further extracted with ethyl acetate. The ethyl acetate layer and the extract were combined, washed with a saturated aqueous solution of sodium chloride, dried over magnesium sulfate and then evaporated under reduced pressure. The precipitated crystals were washed with a mixture of diethyl ether and ethyl acetate and then dried under reduced pressure to give benzhydryl 7-phenylacetamido-3-[N-{2-(N,N-dimethylamino)ethyl}carbamoyloxymethyl]-2-cephem-4-carboxylate (130 mg).

I.R. (Nujol) 3350, 3320, 1780, 1735, 1680, 1655 cm$^{-1}$.

N.M.R. (DMSO-d$_6$, δ) 2.11 (6H, s), 2.22 (2H, t, J=6 Hz), 2.9–3.2 (2H, m), 3.52 (2H, s), 4.52 (2H, s), 5.07 (1H, d, J=4 Hz), 5.20 (1H, s), 5.44 (1H, d,d, J=4 and 8 Hz), 6.71 (1H, s), 6.83 (1H, s), 7.24 (5H, s), 7.28–7.5 (10H, m), 7.0–7.5 (1H, m), 9.14 (1H, d, J=8 Hz).

EXAMPLE 10

The following compounds were obtained according to the similar manners to those in Example 8–9 and optionally by conversion of the products into their desired salts.

(1) Benzhydryl 7-(2,2,2-trichloroethoxycarboxamido)-3-(4-methyl-1-piperazinyl)carbonyloxymethyl-3-cephem-4-carboxylate-1-oxide.

I.R. (Nujol) 3700–3100, 1790, 1760–1660, 1640, 1560–1500 cm$^{-1}$.

N.M.R. (DMSO-d$_6$, δ) 2.2 (3H, s), 2.0–2.43 (4H, m), 3.17–3.5 (4H, m), 3.5–4.0 (2H, broad), 4.5–5.3 (2H, m), 4.93 (2H, s), 5.03 (1H, d, J=4 Hz), 5.7–6.0 (1H, d,d, J=5 and 8 Hz), 7.0 (1H, s), 7.17–7.83 (10H, m), 8.0 (1H, broad)

(2) Benzhydryl 7-phenylacetamido-3-[N-{2-(N,N-dimethylamino)ethyl}carbamoyloxymethyl]-3-cephem-4-carboxylate-1-oxide.

I.R. (Nujol) 3320, 3300, 1790, 1710, 1695, 1645 cm$^{-1}$.

N.M.R. (DMSO-d$_6$, δ) 2.1 (6H, s), 2.0–2.38 (2H, m), 2.8–3.3 (2H, m), 3.6 (2H, s), 3.5–4.0 (2H, m), 4.58, 5.05 (2H, d,d, J=12 Hz), 4.93 (1H, d, J=5 Hz), 5.93 (1H, d,d, J=5 and 8 Hz), 6.93 (1H, s), 7.28 (5H, s), 7.3–7.67 (10H, m), 8.4 (1H, d, J=8 Hz).

(3) Benzhydryl 7-phenylacetamido-3-(4-methyl-1-piperazinyl)carbonyloxymethyl-3-cephem-4-carboxylate-1-oxide.

I.R. (Nujol) 3300, 1790, 1785, 1720, 1700, 1655 cm$^{-1}$.

N.M.R. (DMSO-d$_6$, δ) 2.17 (3H, s), 2.0–2.4 (4H, m), 3.1–3.5 (4H, m), 3.4–4.3 (2H, m), 3.65 (2H, s), 4.6, 5.17 (2H, d,d, J=14 Hz), 4.95 (1H, d, J=5 Hz), 5.93 (1H, d,d, J=5 and 9 Hz), 6.97 (1H, s), 7.1–7.7 (10H, s), 7.32 (5H, s), 8.38 (1H, d, J=9 Hz).

(4) Benzhydryl 7-phenylacetamido-3-[4-(2-hydroxyethyl)-1-piperazinyl]carbonyloxymethyl-3-cephem-4-carboxylate-1-oxide.

I.R. (Nujol) 3600–3100, 1785, 1720, 1690, 1650 cm$^{-1}$.

N.M.R. (DMSO-d$_6$, δ) 2.2–2.6 (6H, m), 3.66 (2H, s), 3.15–3.6 (6H, broad m), 4.6, 5.15 (2H, d,d, J=14 Hz), 5.1 (1H, d, J=5 Hz), 5.92 (1H, d,d, J=5 and 8 Hz), 6.96 (1H, s), 7.3 (5H, s), 7.4 (10H, s), 8.37 (1H, d, J=8 Hz).

(5) Benzhydryl 7-phenylacetamido-3-(4-hydroxypiperidino)carbonyloxymethyl-3-cephem-4-carboxylate-1-oxide.

I.R. (Nujol) 3700–3100, 1780, 1720, 1700–1670, 1650 cm$^{-1}$.

N.M.R. (DMSO-d$_6$, δ) 1.0–2.0 (4H, broad), 2.67–4.0 (7H, broad m), 3.67 (2H, s), 4.6, 5.17 (2H, d,d, J=14 Hz), 4.97 (1H, d, J=4 Hz), 5.95 (1H, d,d, J=4 and 8 Hz), 7.0 (1H, s), 7.33 (5H, s), 7.43 (10H, s), 8.38 (1H, d, J=8 Hz).

(6) Benzhydryl 7-phenylacetamido-3-[N-{(1-ethyl-2-pyrrolidinyl)methyl}carbamoyloxymethyl]-3-cephem-4-carboxylate-1-oxide.

I.R. (Nujol) 3300, 1790, 1740–1660, 1690, 1645 cm$^{-1}$.

N.M.R. (DMSO-d$_6$, δ) 1.03 (3H, t, J=7 Hz), 1.35–1.9 (4H, m), 2.0–2.5 (2H, m), 2.75–3.2 (3H, m), 3.4–4.2 (2H, m), 3.7 (2H, s), 4.63, 5.1 (2H, d,d, J=14 Hz), 5.0 (1H, d, J=5 Hz), 5.95 (1H, d,d, J=5 and 9 Hz), 7.0 (1H, s), 7.33 (5H, s), 7.1–7.8 (10H, m), 8.42 (1H, d, J=9 Hz).

(7) Benzhydryl 7-amino-3-(4-methyl-1-piperazinyl)carbonyloxymethyl-3-cephem-4-carboxylate-1-oxide.

I.R. (Nujol) 3700–3100, 1720, 1700, 1640 cm$^{-1}$.

(8) Benzhydryl 7-[2-methoxyimino-2-(5-amino-1,2,4-thiadiazol-3-yl)acetamido]-3-(4-methyl-1-piperazinyl)carbonyloxymethyl-3-cephem-4-carboxylate-1-oxide (syn isomer).

I.R. (Nujol) 3350, 1790, 1690, 1620, 1460 cm$^{-1}$.

(9) Benzhydryl 7-[2-(2-formamidothiazol-4-yl)acetamido]-3-(4-methyl-1-piperazinyl)carbonyloxymethyl-3-cephem-4-carboxylate-1-oxide.

I.R. (Nujol) 3400, 3300, 1775, 1680, 1530 cm$^{-1}$.

(10) Benzhydryl 7-[D-N-tert-butoxycarbonyl-2-(4-hydroxyphenyl)glycinamido]-3-(4-methyl-1-piperazinyl)carbonyloxymethyl-3-cephem-4-carboxylate-1-oxide.

I.R. (Nujol) 3350, 1790, 1700, 1680, 1610, 1500 cm$^{-1}$.

(11) Benzhydryl 7-[2-propoxyimino-2-(2-formamidothiazol-4-yl)acetamido]-3-(4-methyl-1-piperazinyl)carbonyloxymethyl-3-cephem-4-carboxylate-1-oxide (syn isomer).

I.R. (Nujol) 3250, 1790, 1700, 1550, 1470 cm$^{-1}$.

(12) Benzhydryl 7-[2-methoxyimino-2-(2-furyl)acetamido]-3-(4-methyl-1-piperazinyl)carbonyloxymethyl-3-cephem-4-carboxylate-1-oxide (syn isomer).

I.R. (Nujol) 1790, 1680, 1520 cm$^{-1}$.

(13) Benzhydryl 7-(D-N-tert-butoxycarbonyl-2-phenylglycinamido)-3-(4-methyl-1-piperazinyl)carbonyloxymethyl-3-cephem-4-carboxylate-1-oxide.

I.R. (Nujol) 3300, 1785, 1685, 1490 cm$^{-1}$.

(14) Benzhydryl 7-[2-methoxyimino-2-(2-formamidothiazol-4-yl)acetamido]-3-(4-methyl-1-piperazinyl)[carbonyloxymethyl]-3-cephem-4-carboxylate.trifluoroacetate (syn isomer). This compound was identified with the compound obtained in Example 16 by N.M.R. (15) Benzhydryl 7-[2-methoxyimino-2-(5-amino-1,2,4-thiadiazol-3-yl)acetamido]-3-(4-methyl-1-piperazinyl)-carbonyloxymethyl-3-cephem-4-carboxylate.ditrifluoroacetate (syn isomer).

I.R. (Nujol) 3300, 1790, 1710, 1560, 1470 cm$^{-1}$.

(16) Benzhydryl 7-[2-propoxyimino-2-(2-formamidothiazol-4-yl)acetamido]-3-(4-methyl-1-piperazinyl)carbonyloxymethyl-3-cephem-4-carboxylate.trifluoroacetate (syn isomer).

I.R. (Nujol) 3250, 1790, 1700, 1550, 1470 cm$^{-1}$.

(17) Benzhydryl 7-(2-formamidothiazol-4-yl)acetamido-3-(4-methyl-1-piperazinyl)carbonyloxymethyl-3-cephem-4-carboxylate.trifluoroacetate.

I.R. (Nujol) 3250, 1775, 1700, 1670, 1530 cm$^{-1}$.

(18) Benzhydryl 7-[D-N-tert-butoxycarbonyl-2-(4-hydroxyphenyl)glycinamido]-3-(4-methyl-1-piperazinyl)carbonyloxymethyl-3-cephem-4-carboxylate.trifluoroacetate.

I.R. (Nujol) 3300, 1775, 1700, 1680, 1500 cm$^{-1}$.

(19) Benzhydryl 7-[2-methoxyimino-2-(2-furyl)acetamido]-3-(4-methyl-1-piperazinyl)carbonyloxymethyl-3-cephem-4-carboxylate.trifluoroacetate (syn isomer).

I.R. (Nujol) 3350, 1780, 1700, 1670, 1520 cm$^{-1}$.

(20) Benzhydryl 7-(D-N-tert-butoxycarbonyl-2-phenylglycinamido)3-(4-methyl-1-piperazinyl)carbonyloxymethyl-3-cephem-4-carboxylate.trifluoroacetate.

I.R. (Nujol) 3375, 1780, 1700 cm$^{-1}$.

(21) A mixture of benzhydryl 7-phenylacetamido-3-[N-{2-(N,N-dimethylamino)ethyl}carbamoyloxymethyl]-3-cephem-4-carboxylate and benzhydryl 7-phenylacetamido-3-[N-{2-(N,N-dimethylamino)ethyl}-carbamoyloxymethyl]-2-cephem-4-carboxylate.

I.R. (Nujol) 3320, 3300, 1780, 1710, 1690, 1650, 1540, 1530 cm$^{-1}$.

(22) 7-[2-Methoxyimino-2-(2-formamidothiazol-4-yl)acetamido]-3-(4-methyl-1-piperazinyl)carbonyloxymethyl-3-cephem-4-carboxylic acid.trifluoroacetate (syn isomer).

(23) 7-[2-Methoxyimino-2-(5-amino-1,2,4-thiadiazol-3-yl)acetamido]-3-(4-methyl-1-piperazinyl)carbonyloxymethyl-3-cephem-4-carboxylic acid (syn isomer) which contains about 20% sodium salt thereof.

I.R. (Nujol) 3300, 1770, 1680, 1600, 1530, 1470 cm$^{-1}$.

(24) 7-[2-Propoxyimino-2-(2-formamidothiazol-4-yl)acetamido]-3-(4-methyl-1-piperazinyl)carbonyloxymethyl-3-cephem-4-carboxylic acid.trifluoroacetate (syn isomer).

I.R. (Nujol) 3300, 1790, 1680, 1550, 1470 cm$^{-1}$.

(25) 7-[2-(2-Formamidothiazol-4-yl)acetamido]-3-(4-methyl-1-piperazinyl)carbonyloxymethyl-3-cephem-4-carboxylic acid.trifluoroacetate.

I.R. (Nujol) 1775, 1700, 1665, 1530 cm$^{-1}$.

(26) 7-[2-Methoxyimino-2-(2-furyl)acetamido]-3-(4-methyl-1-piperazinyl)carbonyloxymethyl-3-cephem-4-carboxylic acid.trifluoroacetate (syn isomer).

I.R. (Nujol) 3300, 1785, 1710, 1670, 1520 cm$^{-1}$.

(27) 7-Phenylacetamido-3-[N-{2-(N,N-dimethylamino)ethyl}carbamoyloxymethyl]-3-cephem-4-carboxylic acid.trifluoroacetate.

I.R. (Nujol) 3300, 1780, 1740–1640 cm$^{-1}$.

(28) 7-[2-Methoxyimino-2-(2-aminothiazol-4-yl)acetamido]-3-(4-methyl-1-piperazinyl)carbonyloxymethyl-3-cephem-4-carboxylic acid.dihydrochloride (syn isomer).

N.M.R. (D$_2$O) 3.00 (3H, s), 4.17 (4H, m), 3.55–3.85 (4H, m), 4.07 (3H, s), 4.67–5.00 (2H, ABq, J=14 Hz), 5.25 (1H, d, J=4 Hz), 5.83 (1H, d, J=4 Hz), 7.10 (1H, s).

(29) 7-[2-Propoxyimino-2-(2-aminothiazol-4-yl)acetamido]-3-(4-methyl-1-piperazinyl)carbonyloxymethyl-3-cephem-4-carboxylic acid (syn isomer) which contains about 25% sodium salt thereof.

I.R. (Nujol) 3300, 1770, 1680, 1610, 1540, 1470 cm$^{-1}$.

(30) 7-[2-(2-Aminothiazol-4-yl)acetamido]-3-(4-methyl-1-piperazinyl)carbonyloxymethyl-3-cephem-4-carboxylic acid.dihydrochloride.

I.R. (Nujol) 3250, 1780, 1710, 1690, 1630, 1545 cm$^{-1}$.

(31) 7-[D-2-(4-Hydroxyphenyl)glycinamido]-3-(4-methyl-1-piperazinyl)carbonyloxymethyl-3-cephem-4-carboxylic acid.ditrifluoroacetate.

I.R. (Nujol) 3350, 3170, 1760, 1670, 1590, 1500 cm$^{-1}$.

(32) 7-[D-2-Phenylglycinamido]-3-(4-methyl-1-piperazinyl)carbonyloxymethyl-3-cephem-4-carboxylic acid.trifluoroacetate.formate.

I.R. (Nujol) 3450, 3250, 1780, 1700, 1600 cm$^{-1}$.

(33) Benzhydryl 7-phenylacetamido-3-(4-methyl-1-piperazinyl)carbonyloxymethyl-3-cephem-4-carboxylate.trifluoroacetate.

N.M.R. (DMSO-d$_6$, δ) 2.83 (3H,s), 3.0–4.0 (12H, m), 4.73, 5.03 (2H, d,d, J=14 Hz), 5.17(1H, d, J=5 Hz), 5.83 (1H, d,d, J=5 and 8 Hz), 6.97 (1H, s), 7.32 (5H, s), 7.40 (10H, s), 9.15 (1H, d, J=8 Hz).

(34) 7-phenylacetamido-3-(4-methyl-1-piperazinyl)carbonyloxymethyl-3-cephem-4-carboxylic acid.trifluoroacetate.

I.R. (Nujol) 3700–2200, 1780, 1710, 1670, 1540, 1500, 1290, 1260, 1235, 1180 cm$^{-1}$.

EXAMPLE 11

To a solution of benzhydryl 7-(2,2,2-trichloroethoxycarboxamido)-3-(4-methyl-1-piperazinyl)carbonyloxymethyl-3-cephem-4-carboxylate-1-oxide (15 g) in N,N-dimethylformamide (150 ml) were added acetic acid (15 ml) and zinc powder (7.5 g) with stirring under ice-cooling followed by stirring for 1.5 hours at 5° C. The reaction mixture was filtered to remove remaining zinc powder and thereto were added ethyl acetate (300 ml) and ice-water (300 ml). To the resulting mixture was added sodium bicarbonate (20 g) with stirring so that the pH became about 8.0. After removal of insoluble substances by filtration, the ethyl acetate layer was separated and the remaining aqueous layer was further extracted with ethyl acetate (100 ml×3). The ethyl acetate layer and the extract were combined and added to diluted acetic acid (300 ml). The aqueous layer was separated therefrom, adjusted to about pH 8.0 with an aqueous solution of sodium bicarbonate and then extracted with ethyl acetate three times (300 ml, 200 ml and 100 ml). The extract was washed with an aqueous solution of sodium chloride (100 ml×3), dried over magnesium sulfate and evaporated. The residue was pulverized in diisopropyl ether, collected by filtration and then dried under reduced pressure to give benzhydryl 7-amino-3-(4-methyl-1-piperazinyl)carbonyloxymethyl-3-cephem-4-carboxylate-1-oxide (4.6 g).

I.R. (Nujol) 3700–3100, 1780, 1720, 1700, 1640 cm$^{-1}$.

N.M.R. (DMSO-d$_6$, δ) 1.8–2.4 (4H, m), 2.15 (3H, s), 3.0–3.4 (4H, m), 3.56, 3.92 (2H, d,d, J=16 and 36 Hz), 4.56, 5.03 (2H, d,d, J=12 and 50 Hz), 4.74 (1H, d, J=4 Hz), 4.88 (1H, d, J=4 Hz), 6.91 (1H, s), 7.0–7.6 (10H, m).

EXAMPLE 12

A mixture of benzhydryl 7-amino-3-(4-methyl-1-piperazinyl)carbonyloxymethyl-3-cephem-4-carboxylate-1-oxide (1.33 g) and trimethylsilylacetamide (0.65 g) in dry methylene chloride (40 ml) was stirred for 2.5 hours at room temperature and then cooled to −20° C. (A solution). On the other hand, to a mixture of 2-methoxyimino-2-(5-amino-1,2,4-thiadiazol-3-yl)acetic acid (syn isomer) (0.50 g) in dry methylene chloride (12.5 ml) was added phosphorus oxychloride (1.6 ml) under ice-water cooling followed by stirring for 2 hours at room temperature. To the mixture was added a solution of N,N-dimethylformamide (0.99 ml) in dry methylene chloride (2 ml) followed by stirring for 50 minutes under ice-water cooling. Thus obtained solution was added to the A solution obtained above, followed by stirring for an hour at −30° to −20° C. The reaction mixture was poured into a mixture of a saturated aqueous solution of sodium bicarbonate (35 ml) and water (35 ml). The methylene chloride layer was separated therefrom and the remaining aqueous layer was further extracted with methylene chloride (50 ml×2). The methylene chloride layer and the extract were combined, washed with a saturated aqueous solution of sodium chloride, dried over magnesium sulfate, treated with activated charcoal and evaporated under reduced pressure. The residue was washed with diethyl ether and dried to give benzhydryl 7-[2-methoxyimino-2-(5-amino-1,2,4-thiadiazol-3-yl)acetamido]-3-(4-methyl-1-piperazinyl)carbonyloxymethyl-3-cephem-4-carboxylate-1-oxide (syn isomer) (1.3 g).

I.R. (Nujol) 3350, 1790, 1690, 1620, 1460 cm$^{-1}$.

N.M.R. (DMSO-d$_6$, δ) 2.5 (3H, s), 2.60–2.93 (4H, m), 3.27–3.67 (4H, m), 3.70–3.90 (2H, broad s), 3.93 (3H, s), 4.03–4.40 (2H, broad s), 4.63, 5.17 (2H, ABq, J=12 Hz), 5.03 (1H, d, J=4 Hz), 6.07 (1H, d,d, J=4 and 8 Hz), 6.93 (1H, s), 7.13–7.67 (10H, m), 9.10 (1H, d, J=8 Hz).

EXAMPLE 13

A mixture of 2-(2-formamidothiazol-b 4-yl)acetic acid (0.70 g), 2.6-lutidine (0.44 ml), triethylamine (0.05 ml) and pivaloyl chloride (457 mg) in dry methylene chloride (10 ml) was stirred at −15° C. for 20 minutes, at 12° C. for 20 minutes and at 22° C. for a further 40 minutes. A mixture of benzhydryl 7-amino-3-(4-methyl-1-piperazinyl)carbonyloxymethyl-3-cephem-4-carboxylate-1-oxide (1.7 g) in methylene chloride (20 ml) was cooled to −30° C. and thereto was added the acid anhydride solution obtained above followed by stirring at −20° to −10° C. for an hour and at −10° C. to ambient temperature for a further one hour. The reaction mixture was evaporated and to the residue was added ethyl acetate (20 ml) and water (10 ml) followed by stirring. Insoluble substances were collected by filtration, washed with water and ethyl acetate and then dried under reduced pressure to give benzhydryl 7-[2-(2-formamidothiazol-4-yl)acetamido]-3-(4-methyl-1-piperazinyl)carbonyloxymethyl-3-cephem-4-carboxylate-1-oxide (1.75 g).

I.R. (Nujol) 3400, 3300, 1775, 1680, 1530 cm$^{-1}$.

N.M.R. (DMSO-d$_6$, δ) 2.62 (3H, s), 2.8–3.2 (4H, m), 3.4–4 (6H, m), 3.68 (2H, s), 4.62,5.16 (2H, ABq, J=4 Hz), 4.98 (1H, d, J=5 Hz), 6.02 (1H, d,d, J=5 and 10 Hz), 6.94 (1H, s), 7.02 (1H, s), 7.37 (10H, broad s), 8.16 (1H, d, J=10 Hz), 8.47 (1H, s).

EXAMPLE 14

A mixture of D-N-tert-butoxycarbonyl-2-(4-hydroxyphenyl)glycine (1.19 g), 2,6-lutidine (0.52 ml) and benzoyl chloride (0.52 ml) in dry methylene chloride (12 ml) was stirred for an hour at −20° to −10° C., and all at once added to a mixture of benzhydryl 7-amino-3-(4-methyl-1-piperazinyl)-carbonyloxymethyl-3-cephem-4-carboxylate-1-oxide (2 g) and 2,6-lutidine (0.1 ml) in methylene chloride (20 ml) followed by stirring for 2 hours at −20° to −10° C. The reaction mixture was evaporated and to the residue were added water and ethyl acetate. The ethyl acetate layer was separated and the remaining aqueous layer was further extracted with ethyl acetate. The ethyl acetate layers were combined, washed with an aqueous solution of sodium bicarbonate and a saturated aqueous solution of sodium chloride, dried over magnesium sulfate, treated with activated charcoal and then filtered. The filtrate was evaporated and the residue was pulverized in diethyl ether to give benzhydryl 7-[D-N-tert-butoxycarbonyl-2-(4-hydroxyphenyl)glycinamido]-3-(4-methyl-1-piperazinyl)carbonyloxymethyl-3-cephem-4-carboxylate-1-oxide (2.4 g).

I.R. (Nujol) 3350, 1790, 1700, 1680, 1610, 1500.

N.M.R. (DMSO-d$_6$+D$_2$O, δ) 1.39 (9H, s), 2.15 (3H, s), 2.1–2.35 (4H, m), 3.15–3.4 (6H, m), 4.9 (2H, ABq, J=13 Hz), 4.91 (1H, d, J=5 Hz), 5.26 (1H, s), 6.0 (1H, d, J=5 Hz), 6.94 (1H, s), 6.96 (4H, ABq, J=9 Hz), 7.36 (10H, broad s).

EXAMPLE 15

The following compounds were obtained according to the similar manners to those in Examples 12–14 and optionally by conversion of the products into their desired salts.

(1) Benzhydryl 7-[2-propoxyimino-2-(2-formamidothiazol-4-yl)acetamido]-3-(4-methyl-1-piperazinyl)carbonyloxymethyl-3-cephem-4-carboxylate-1-oxide (syn isomer) (1.6 g).

I.R. (Nujol) 3250, 1790, 1700, 1550, 1470 cm$^{-1}$.

N.M.R. (DMSO-d$_6$, δ) 0.92 (3H, t, J=8 Hz), 1.46–1.86 (2H, m), 2.26 (3H, s), 2.30–2.44 (4H, m), 3.20–3.48 (4H, m), 3.88–4.14 (4H, m), 4.64, 5.16 (2H, ABq, J=14 Hz), 5.08 (1H, d, J=4 Hz), 6.10 (1H, d,d, J=4 and 8 Hz), 6.96 (1H, s), 7.12–7.68 (11H, m), 8.52 (1H, s), 9.02 (1H, d, J=8 Hz).

(2) Benzhydryl 7-[2-methoxyimino-2-(2-furyl)acetamido]-3-(4-methyl-1-piperazinyl)carbonyloxymethyl-3-cephem-4-carboxylate-1-oxide (syn isomer).

I.R. (Nujol) 1790, 1680, 1520 cm$^{-1}$.

N.M.R. (DMSO-d$_6$, δ) 2.15 (3H, s), 2.1–2.4 (4H, m), 3.2–3.6 (6H, m), 3.90 (3H, s), 4.60, 5.12 (2H, ABq, J=14 Hz), 5.03 (1H, d, J=5 Hz), 6.0 (1H, d,d, J=5 and 7 Hz), 6.5–6.8 (2H, m), 6.94 (1H, s), 7.4 (10H, broad s), 7.80 (1H, s), 9.30 (1H, d, J=7 Hz).

(3) Benzhydryl 7-(D-N-tert-butoxycarbonyl-2-phenylglycinamido)-3-(4-methyl-1-piperazinyl)carbonyloxymethyl-3-cephem-4-carboxylate-1-oxide.

I.R. (Nujol) 3300, 1785, 1685, 1490 cm$^{-1}$.

N.M.R. (DMSO-d$_6$, δ) 1.40 (9H, s), 2.20 (3H, s), 2.2–2.4 (4H, m), 3.2–3.9 (6H, m), 4.58, 5.15 (2H, ABq, J=13 Hz), 4.92 (1H, d, J=5 Hz), 5.37 (1H, d, J=8 Hz), 6.0 (1H, d,d, J=5 and 7 Hz), 6.95 (1H, s), 7.4 (15H, broad s), 8.34 (1H, d, J=7 Hz).

(4) Benzhydryl 7-[2-methoxyimino-2-(2-formamidothiazol-4-yl)acetamido]-3-(1-imidazolyl)carbonyloxymethyl-3-cephem-4-carboxylate (syn isomer).

I.R. (Nujol) 3700–2400, 1770, 1760, 1720, 1660, 1535, 1485, 1450, 1390, 1370, 1310, 1280, 1230, 1160, 1090, 1060, 1030, 995 cm$^{-1}$.

(5) A mixture of benzhydryl 7-(2,2,2-trichloroethoxycarboxamido)-3-(1-imidazolyl)carbonyloxymethyl-3-cephem-4-carboxylate and benzhydryl 7-(2,2,2-trichloroethoxycarboxamido)-3-(1-imidazolyl)carbonyloxymethyl-2-cephem-4-carboxylate.

I.R. (Nujol) 3600–3450, 3400–3100, 1800–1700, 1550–1500 cm$^{-1}$.

(6) Benzhydryl 7-phenylacetamido-3-(1-imidazolyl)carbonyloxymethyl-2-cephem-4-carboxylate.

I.R. (Nujol) 3330, 3130, 3060, 3030, 1775, 1760, 1740, 1650, 1530, 1500 cm$^{-1}$.

(7) Benzhydryl 7-[2-methoxyimino-2-(2-formamidothiazol-4-yl)acetamido]-3-(1-imidazolyl)carbonyloxymethyl-3-cephem-4-carboxylate-1-oxide (syn isomer).

I.R. (Nujol) 3700–3300, 1790, 1760, 1720, 1680, 1660, 1520 cm$^{-1}$.

(8) Benzhydryl 7-(2,2,2-trichloroethoxycarboxamido)-3-(1-imidazolyl)carbonyloxymethyl-3-cephem-4-carboxylate-1-oxide.

I.R. (Nujol) 3500–3100, 1790, 1760–1700, 1520 cm$^{-1}$.

(9) Benzhydryl 7-phenylacetamido-3-(1-imidazolyl)carbonyloxymethyl-3-cephem-4-carboxylate-1-oxide.

I.R. (Nujol) 3300, 3600–3100, 1790, 1765, 1710, 1645 cm$^{-1}$.

(10) Benzhydryl-7-[2-methoxyimino-2-(2-formamidothiazol-4-yl)acetamido]-3-(4-methyl-1-piperazinyl)carbonyloxymethyl-3-cephem-4-carboxylate-1-oxide (syn isomer). This compound was identified with the compound obtained in Example 8 by N.M.R.

(11) Benzhydryl 7-phenylacetamido-3-[N-{2-(N,N-dimethylamino)ethyl}carbamoyloxymethyl]-2-cephem-4-carboxylate.

I.R. (Nujol) 3350, 3320, 1780, 1735, 1680, 1655 cm$^{-1}$.

(12) Benzhydryl 7-(2,2,2-trichloroethoxycarboxamido)-3-(4-methyl-1-piperazinyl)carbonyloxymethyl-3-cephem-4-carboxylate-1-oxide.

I.R. (Nujol) 3700–3100, 1790, 1760–1660, 1640, 1560–1500 cm$^{-1}$.

(13) Benzhydryl 7-phenylacetamido-3-[N-{2-(N,N-dimethylamino)ethyl}carbamoyloxymethyl]-3-cephem-4-carboxylate-1-oxide.

I.R. (Nujol) 3320, 3300, 1790, 1710, 1695, 1645 cm$^{-1}$.

(14) Benzhydryl 7-phenylacetamido-3-(4-methyl-1-piperazinyl)carbonyloxymethyl-3-cephem-4-carboxylate-1-oxide.

I.R. (Nujol) 3300, 1790, 1785, 1720, 1700, 1655 cm$^{-1}$.

(15) Benzhydryl 7-phenylacetamido-3-[4-(2-hydroxyethyl)-1-piperazinyl]carbonyloxymethyl-3-cephem-4-carboxylate-1-oxide.

I.R. (Nujol) 3600-3100, 1785, 1720, 1690, 1650 cm$^{-1}$.

(16) Benzhydryl 7-phenylacetamido-3-(4-hydroxypiperidino)carbonyloxymethyl-3-cephem-4-carboxylate-1-oxide.

I.R. (Nujol) 3700-3100, 1780, 1720, 1700-1670, 1650 cm$^{-1}$.

(17) Benzhydryl 7-phenylacetamido-3-[N-{(1-ethyl-2-pyrrolidinyl)methyl}carbamoyloxymethyl]-3-cephem 4-carboxylate-1-oxide.

I.R. (Nujol) 3300, 1790, 1740-1660, 1690, 1645 cm$^{-1}$.

(18) Benzhydryl 7-[2-methoxyimino-2-(2-formamidothiazol-4-yl)acetamido]-3-(4-methyl-1-piperazinyl)carbonyloxymethyl-3-cephem-4-carboxylate.trifluoroacetate (syn isomer). This compound was identified with the compound obtained in Example 16 by N.M.R.

(19) Benzhydryl 7-[2-methoxyimino-2-(5-amino-1,2,4-thiadiazol-3-yl)acetamido]-3-(4-methyl-1-piperazinyl)carbonyloxymethyl-3-cephem-4-carboxylate.ditrifluoroacetate (syn isomer).

I.R. (Nujol) 3300, 1790, 1710, 1560, 1470 cm$^{-1}$.

(20) Benzhydryl 7-[2-propoxyimino-2-(2-formamidothiazol-4-yl)acetamido]-3-(4-methyl-1-piperazinyl)carbonyloxymethyl-3-cephem-4-carboxylate.trifluoroacetate (syn isomer).

I.R. (Nujol) 3250, 1790, 1700, 1550, 1470 cm$^{-1}$.

(21) Benzhydryl 7-(2-formamidothiazol-4-yl)acetamido-3-(4-methyl-1-piperazinyl)carbonyloxymethyl-3-cephem-4-carboxylate.trifluoroacetate I.R. (Nujol) 3250, 1775, 1700, 1670, 1530 cm$^{-1}$.

(22) Benzhydryl 7-[D-N-tert-butoxycarbonyl-2-(4-hydroxyphenyl)glycinamido]-3-(4-methyl-1-piperazinyl)carbonyloxymethyl-3-cephem-4-carboxylate.trifluoroacetate.

I.R. (Nujol) 3300, 1775, 1700, 1680, 1500 cm$^{-1}$.

(23) Benzhydryl 7-[2-methoxyimino-2-(2-furyl)acetamido]-3-(4-methyl-1-piperazinyl)carbonyloxymethyl-3-cephem-4-carboxylate.trifluoroacetate (syn isomer).

I.R. (Nujol) 3350, 1780, 1700, 1670, 1520 cm$^{-1}$.

(24) Benzhydryl 7-(D-N-tert-butoxycarbonyl-2-phenylglycinamido)-3-(4-methyl-1-piperazinyl)carbonyloxymethyl-3-cephem-4-carboxylate.trifluoroacetate.

I.R. (Nujol) 3375, 1780, 1700 cm$^{-1}$.

(25) A mixture of benxhydryl 7-phenylacetamido-3-[N-{2-(N,N-dimethylamino)ethyl}carbamoyloxymethyl]-3-cephem-4-carboxylate and benzhydryl 7-phenylacetamido-3-[N-{2-(N,N-dimethylamino)ethyl}-carbamoyloxymethyl]-2-cephem-4-carboxylate.

I.R. (Nujol) 3320, 3300, 1780, 1710, 1690, 1650, 1540, 1530 cm$^{-1}$.

(26) 7-[2-Methoxyimino-2-(2-formaidothiazol-4-yl)acetamido]-3-(4-methyl-1-piperazinyl)carbonyloxymethyl-3-cephem-4-carboxylic acid.trifluoroacetate (syn isomer).

I.R. (Nujol) 3300, 1770, 1680, 1600, 1530, 1470 cm$^{-1}$.

(27) 7-[2-Methoxyimino-2-(5-amino-1,2,4-thiadiazol-3-yl)acetamido]-3-(4-methyl-1-piperazinyl)carbonyloxymethyl-3-cephem-4-carboxylic acid (syn isomer) which contains about 20% sodium salt thereof.

I.R. (Nujol) 3300, 1770, 1680, 1600, 1530, 1470 cm$^{-1}$.

(28) 7-[2-Propoxyimino-2-(2-formamidothiazol-4-yl)acetamido]-3-(4-methyl-1-piperazinyl)carbonyloxymethyl-3-cephem-4-carboxylic acid.trifluoroacetate (syn isomer).

I.R. (Nujol) 3300, 1790, 1680, 1550, 1470 cm$^{-1}$.

(29) 7-[2-(2-Formamidothiazol-4-yl)acetamido]-3-(4-methyl-1-piperazinyl)carbonyloxymethyl-3-cephem-4-carboxylic acid.trifluoroacetate.

I.R. (Nujol) 1775, 1700, 1665, 1530 cm$^{-1}$.

(30) 7-[2-Methoxyimino-2-(2-furyl)acetamido]-3-(4-methyl-1-piperazinyl)carbonyloxymethyl-3-cephem-4-carboxylic acid.trifluoroacetate (syn isomer).

I.R. (Nujol) 3300, 1785, 1710, 1670, 1520 cm$^{-1}$.

(31) 7-Phenylacetamido-3-[N-{2-(N,N-dimethylamino)ethyl}carbamoyloxymethyl]-3-cephem-4-carboxylic acid.trifluoroacetate.

I.R. (Nujol) 3300, 1780, 1740-1640 cm$^{-1}$.

(32) 7-[2-Methoxyimino-2-(2-aminothiazol-4-yl)acetamido]-3-(4-methyl-1-piperazinyl)carbonyloxymethyl-3-cephem-4-carboxylic acid.dihydrochloride (syn isomer).

N.M.R. (D$_2$O) 3.00 (3H, s), 4.17 (4H, m), 3.55-3.85 (4H, m) 4.07 (3H, s), 4.67-5.00 (2H, ABq, J=14 Hz), 5.25 (1H, d, J=4 Hz), 5.83 (1H, d, J=4 Hz), 7.10 (1H, s).

(33) 7-[2-Propoxyimino-2-(2-aminothiazol-4-yl)acetamido]-3-(4-methyl-1-piperazinyl)carbonyloxymethyl-3-cephem-4-carboxylic acid (syn isomer) which contains about 25% sodium salt thereof.

I.R. (Nujol) 3300, 1770, 1680, 1610, 1540, 1470 cm$^{-1}$.

(34) 7-[2-(2-Aminothiazol-4-yl)acetamido]-3-(4-methyl-1-piperazinyl)carbonyloxymethyl-3-cephem-4-carboxylic acid.dihydrochloride.

I.R. (Nujol) 3250, 1780, 1710, 1690, 1630, 1545 cm$^{-1}$.

(35) 7-[D-2-(4-Hydroxyphenyl)glycinamido]-3-(4-methyl-1-piperazinyl)carbonyloxymethyl-3-cephem-4-carboxylic acid.ditrifluoroacetate.

I.R. (Nujol) 3350, 3170, 1760, 1670, 1590, 1500 cm$^{-1}$.

(36) 7-[D-2-Phenylglycinamido]-3-(4-methyl-1-piperazinyl)carbonyloxymethyl-3-cephem-4-carboxylic acid.trifluoroacetate.formate.

I.R. (Nujol) 3450, 3250, 1780, 1700, 1600 cm$^{-1}$.

(37) Benzhydryl 7-phenylacetamido-3-(4-methyl-1-piperazinyl)carbonyloxymethyl-3-cephem-4-carboxylate.trifluoroacetate.

N.M.R. (DMSO-d$_6$, δ) 2.83 (3H, s), 3.0-4.0 (12H, m), 4.73, 5.03 (2H, d,d, J=14 Hz), 5.17 (1H, d, J=5 Hz), 5.83 (1H, d,d, J=5 and 8 Hz), 6.97 (1H, s), 7.32 (5H, s), 7.40 (10H, s), 9.15 (1H, d, J=8 Hz).

(38) 7-phenylacetamido-3-(4-methyl-1-piperazinyl)-carbonyloxymethyl-3-cephem-4-carboxylic acid.trifluoroacetate.

I.R. (Nujol) 3700-2200, 1780, 1710, 1670, 1540, 1500, 1290, 1260, 1235, 1180 cm$^{-1}$.

EXAMPLE 16

In a solution of benzhydryl 7-[2-methoxyimino-2-(2-formamidothiazol-4-yl)acetamido]-3-(4-methyl-1-piperazinyl)carbonyloxymethyl-3-cephem-4-carboxylate-1-oxide (syn isomer) (1.5 g) in a mixture of tetrahydrofuran (30 ml) and acetone (15 ml) was dissolved sodium iodide (1.44 g) under ice-cooling and thereto was at a time added trifluoroacetic anhydride (2.04 ml) followed by stirring for 2.5 hours. The reaction mixture was evaporated and to the residue were added ethyl acetate and water. The ethyl acetate layer was separated, washed with 5% aqueous solution of sodium thiosulfate, and an aqueous solution of sodium chloride, dried over magnesium sulfate, treated with activated charcoal and then evaporated to give benzhydryl 7-[2-methoxyimino-2-(2-formamidothiazol-4-yl)acetamido]-3-(4-methyl-1-piperazinyl)carbonyloxymethyl]-3-cephem-4-carboxylate.trifluoroacetate (syn isomer) (1.5 g).

N.M.R. (DMSO-$d_6$, $\delta$) 2.83 (3H, s), 3.0–3.5 (4H, broad), 3.5–4.0 (6H, broad), 3.97 (3H, s), 4.73, 5.07 (2H, d,d, J=14 Hz), 5.27 (1H, d, J=4 Hz), 5.97 (1H, d,d, J=4 and 8 Hz), 7.0 (1H, s), 7.2–7.83 (10H, m), 9.83 (1H, d, J=8 Hz).

EXAMPLE 17

A mixture of benzhydryl 7-[2-methoxyimino-2-(5-amino-1,2,4-thiadiazol-3-yl)acetamido]-3-(4-methyl-1-piperazinyl)carbonyloxymethyl-3-cephem-4-carboxylate-1-oxide (syn isomer) (1.25 g) in a mixture of dry acetone (150 ml) and tetrahydrofuran (50 ml) was stirred under ice-water cooling and thereto were added sodium iodide (620 mg) and trifluoroacetic anhydride (0.59 ml) followed by stirring for 4 hours at the same temperature. The reaction mixture was evaporated under reduced pressure and to the residue were added ethyl acetate (60 ml) and water (20 ml). The ethyl acetate layer was separated therefrom, washed with 5% aqueous solution of sodium thiosulfate (20 ml×3), and a saturated aqueous solution of sodium chloride, dried over magnesium sulfate, treated with activated charcoal and then evaporated under reduced pressure. The residue was washed with diethyl ether and dried to give benzhydryl 7-[2-methoxyimino-2-(5-amino-1,2,4-thiadiazol-3-yl)acetamido]-3-(4-methyl-1-piperazinyl)-carbonyloxymethyl-3-cephem-4-carboxylate.ditrifluoroacetate (syn isomer) (0.9 g).

I.R. (Nujol) 3300, 1790, 1710, 1560, 1470 cm$^{-1}$.

N.M.R. (DMSO-$d_6$, $\delta$) 2.80 (3H, s), 2.93–3.47 (4H, m), 3.47–3.90 (6H, m), 3.97 (3H, s), 4.70, 5.07 (2H, ABq, J=14 Hz), 5.23 (1H, d, J=4 Hz), 5.53–6.43 (2H, broad s), 6.17 (1H, d,d, J=4 and 8 Hz), 6.93 (1H, s), 7.20–7.67 (10H, m), 9.70 (1H, d, J=8 Hz).

EXAMPLE 18

The following compounds were obtained according to the similar manners to those in Example 16–17 and optionally by conversion of the products into their desired salts.

(1) Benzhydryl 7-[2-propoxyimino-2-(2-formamidothiazol-4-yl)acetamido]-3-(4-methyl-1-piperazinyl)carbonyloxymethyl-3-cephem-4-carboxylate.trifluoroacetate (syn isomer) (1.3 g).

I.R. (Nujol) 3250, 1790, 1700, 1550, 1470 cm$^{-1}$.

N.M.R. (DMSO-$d_6$, $\delta$) 0.88 (3H, t, J=8Hz), 1.23–2.00 (2H, m), 2.75 (3H, s), 2.90–3.33 (4H, m), 3.37–3.77 (6H, m), 4.05 (2H, t, J=8Hz), 4.70–4.93 (2H, broad), 5.20 (1H, d, J=4Hz), 5.73–6.10 (1H, broad), 6.90 (1H, s), 7.10–7.63 (11H, m), 8.53 (1H, s), 9.53–9.83 (1H, broad).

(2) Benzhydryl 7-(2-formamidothiazol-4-yl)acetamido-3-(4-methyl-1-piperazinyl)carbonyloxymethyl-3-cephem-4-carboxylate.trifluoroacetate.

I.R. (Nujol) 3250, 1775, 1700, 1670, 1530 cm$^{-1}$.

N.M.R. (DMSO-$d_6$, $\delta$) 2.77 (3H, s), 3–3.3 (4H, m), 3.4–3.8 (8H, m), 4.57, 4.99 (2H, ABq, J=13Hz), 5.15 (1H, d, J=5Hz), 5.82 (1H, d,d, J=5 and 9Hz), 6.93 (1H, s), 6.96 (1H, s), 7.37 (10H, broad s), 8.47 (1H, s), 9.0 (1H, d, J=9Hz).

(3) Benzhydryl 7-[D-N-tert-butoxycarbonyl-2-(4-hydroxyphenyl)glycinamido]-3-(4-methyl-1-piperazinyl)-carbonyloxymethyl-3-cephem-4-carboxylate.trifluoroacetate.

I.R. (Nujol) 3300, 1775, 1700, 1680, 1500 cm$^{-1}$.

N.M.R. (DMSO-$d_6$, $\delta$) 1.3 (9H, s), 2.8 (3H, s), 3.1–3.8 (10H, m), 4.62 (2H, ABq, J=13Hz), 5.08 (1H, d, J=5Hz), 5.2 (1H, s), 5.8 (1H, d, J=5Hz), 6.95 (1H, s), 6.97 (4H, ABq, J=9Hz), 7.4 (10H, broad s).

(4) Benzhydryl 7-[2-methoxyimino-2-(2-furyl)-acetamido]-3-(4-methyl-1-piperazinyl)carbonyloxymethyl-3-cephem-4-carboxylate.trifluoroacetate (syn isomer).

I.R. (Nujol) 3350, 1780, 1700, 1670, 1520 cm$^{-1}$.

N.M.R. (DMSO-$d_6$, $\delta$) 2.80 (3H, s), 3.1–3.8 (10H, m), 3.94 (3H, s), 4.72–5.05 (2H, ABq, J=14 Hz), 5.26 (1H, d, J=5 Hz), 5.96 (1H, d,d, J=5 and 8 Hz), 6.6–6.9 (2H, m), 6.97 (1H, s), 7.4 (10H, broad s), 7.86 (1H, s), 9.82 (1H, d, J=8 Hz).

(5) Benzhydryl 7-(D-N-tert-butoxycarbonyl-2-phenylglycinamido)-3-(4-methyl-1-piperazinyl)-carbonyloxymethyl-3-cephem-4-carboxylate.trifluoroacetate.

I.R. (Nujol) 3375, 1780, 1700 cm$^{-1}$.

N.M.R. (DMSO-$d_6$, $\delta$) 1.43 (9H, s), 2.81 (3H, s), 3.1–3.4 (4H, m), 3.4–3.8 (6H, m), 4.7, 5.0 (2H, ABq, J=12 Hz), 5.10 (1H, d, J=5 Hz), 5.40 (1H, d, J=8 Hz), 5.87 (1H, d,d, J=5 and 8 Hz), 6.98 (1H, s), 7.43 (15H, broad s), 9.23 (1H, d, J=8 Hz).

(6) A mixture of benzhydryl 7-phenylacetamido-3-[N-{2-(N,N-dimethylamino)ethyl}carbamoyloxymethyl]-3-cephem-4-crboxylate and benzhydryl 7-phenylacetamido-3-[N-{2-(N,N-dimthylamino)ethyl}-carbamoyloxymethyl]-2-cephem-4-carboxylate.

I.R. (Nujol) 3320, 3300, 1780, 1710, 1690, 1650, 1540, 1530 cm$^{-1}$.

N.M.R. (DMSO-$d_6$, $\delta$) 2.17 (6H, s), 2.1–2.5 (2H, m), 2.9–3.3 (2H, m), 3.57 (2H, s), 3.5–4.0 (2H, broad), 4.5–5.0 (2H, m), 5.1 (1H, d, J=4 Hz), 5.23 (1H, s), 5.33–5.8 (1H, m), 6.77 (1H, s), 6.9 (1H, s), 7.3 (5H, s), 7.4 (10H, s), 7.0–7.5 (1H, m), 9.13, 9.2 (1H, d, J=8 Hz).

(7) Benzhydryl 7-[2-methoxyimino-2-(2-formamidothiazol-4-yl)acetamido]-3-(1-imidazolyl)carbonyloxymethyl-3-cephem-4-carboxylate (syn isomer).

I.R. (Nujol) 3700–2400, 1770, 1760, 1720, 1660, 1535, 1485, 1450, 1390, 1370, 1310, 1280, 1230, 1160, 1090, 1060, 1030, 995 cm$^{-1}$.

(8) 7-[2-Methoxyimino-2-(2-formamidothiazol-4-yl)-acetamido]-3-(4-methyl-1-piperazinyl)carbonyloxymethyl-3-cephem-4-carboxylic acid.trifluoroacetate (syn isomer).

(9) 7-[2-Methoxyimino-2-(5-amino-1,2,4-thiadiazol-3-yl)acetamido]-3-(4-methyl-1-piperazinyl)-carbonyloxymethyl-3-cephem-4-carboxylic acid (syn isomer) which contains about 20% sodium salt thereof.

I.R. (Nujol) 3300, 1770, 1680, 1600, 1530, 1470 cm$^{-1}$.

(10) 7-[2-Propoxyimino-2-(2-formamidothiazol-4-yl)acetamido]-3-(4-methyl-1-piperazinyl)carbonyloxymethyl-3-cephem-4-carboxylic acid.trifluoroacetate (syn isomer).

I.R. (Nujol) 3300, 1790, 1680, 1550, 1470 cm$^{-1}$.

(11) 7-[2-(2-Formamidothiazol-4-yl)acetamido]-3-(4-methyl-1-piperazinyl)carbonyloxymethyl-3-cephem-4-carboxylic acid.trifluoroacetate.

I.R. (Nujol) 1775, 1700, 1665, 1530 cm$^{-1}$.

(12) 7-[2-Methoxyimino-2-(2-furyl)acetamido]-3-(4-methyl-1-piperazinyl)carbonyloxymethyl-3-cephem-4-carboxylic acid trifluoroacetate (syn isomer).

I.R. (Nujol) 3300, 1785, 1710, 1670, 1520 cm$^{-1}$.

(13) 7-Phenylacetamido-3-[N-{2-(N,N-dimethylamino)-ethyl}carbamoyloxymethyl]-3-cephem-4-carboxylic acid: trifluoroacetate.

I.R. (Nujol) 3300, 1780, 1740–1640 cm$^{-1}$.

(14) 7-[2-Methoxyimino-2-(2-aminothiazol-4-yl)-acetamido]-3-(4-methyl-1-piperazinyl)carbonyloxymethyl-3-cephem-4-carboxylic acid.dihydrochloride (syn isomer).

N.M.R. (D$_2$O) 3.00 (3H, s), 4.17 (4H, m), 3.55–3.85 (4H, m), 4.07 (3H, s), 4.67–5.00 (2H, ABq, J=14 Hz), 5.25 (1H, d, J=4 Hz), 5.83 (1H, d, J=4 Hz), 7.10 (1H, s).

(15) 7-[2-Propoxyimino-2-(2-aminothiazol-4-yl)-acetamido]-3-(4-methyl-1-piperazinyl)carbonyloxymethyl-3-cephem-4-carboxylic acid (syn isomer) which contains about 25% sodium salt thereof.

I.R. (Nujol) 3300, 1770, 1680, 1610, 1540, 1470 cm$^{-1}$.

(16) 7-[2-(2-Aminothiazol-4-yl)acetamido]-3-(4-methyl-1-piperazinyl)carbonyloxymethyl-3-cephem-4-carboxylic acid. dihydrochloride.

I.R. (Nujol) 3250, 1780, 1710, 1690, 1630, 1545 cm$^{-1}$.

(17) 7-[D-2-(4-Hydroxyphenyl)glycinamido]-3-(4-methyl-1-piperazinyl)carbonyloxymethyl-3-cephem-4-carboxylic acid.ditrifluoroacetate.

I.R. (Nujol) 3350, 3170, 1760, 1670, 1590, 1500 cm$^{-1}$.

(18) 7-[D-2-Phenylglycinamido]-3-(4-methyl-1-piperazinyl)carbonyloxymethyl-3-cephem-4-carboxylic acid.trifluoroacetate.formate.

I.R. (Nujol) 3450, 3250, 1780, 1700, 1600 cm$^{-1}$.

(19) Benzhydryl 7-phenylacetamido-3-(4-methyl-1-piperazinyl)carbonyloxymethyl-3-cephem-4-carboxylate.trifluoroacetate.

N.M.R. (DMSO-d$_6$,δ) 2.83 (3H, s), 3.0–4.0 (12H, m), 4.73, 5.03 (2H, d,d, J=14 Hz), 5.17 (1H, d, J=5 Hz), 5.83 (1H, d,d, J=5 and 8 Hz), 6.97 (1H, s), 7.32 (5H, s), 7.40 (10H, s), 9.15 (1H, d, J=8 Hz).

(20) 7-phenylacetamido-3-(4-methyl-1-piperazinyl)-carbonyloxymethyl-3-cephem-4-carboxylic acid.trifluoroacetate.

I.R. (Nujol) 3700–2200, 1780, 1710, 1670, 1540, 1500, 1290, 1260, 1235, 1180 cm$^{-1}$.

EXAMPLE 19

To a solution of benzhydryl 7-[2-methoxyimino-2-(2-formamidothiazol-4-yl)acetamido]-3-(4-methyl-1-piperazinyl)carbonyloxymethyl-3-cephem-4-carboxylate.trifluoroacetate (syn isomer)(1.4 g) in methylene chloride (30 ml) were added anisole (1.4 ml) and trifluoroacetate acid (1.83 ml) with stirring under ice-cooling and the stirring was continued for 4 hours at 5° C. The reaction mixture was evaporated and the residual oil was pulverized in diethyl ether, collected by filtration and then dried to give 7-[2-methoxyimino-2-(2-formamidothiazol-4-yl)acetamido]-3-(4-methyl-1-piperazinyl)carbonyloxymethyl-3-cephem-4-carboxylic acid.trifluoroacetate (syn isomer)(1.1 g).

EXAMPLE 20

To a mixture of benzhydryl 7-[2-methoxyimino-2-(5-amino-1,2,4-thiadiazol-3-yl)acetamido]-3-(4-methyl-1-piperazinyl)carbonyloxymethyl-3-cephem-4-carboxylate.ditrifluoroacetate (syn isomer)(0.9 g) in dry methylene chloride (30 ml) were added anisole (0.9 ml) and trifluoroacetic acid (1.41 ml) under ice-water cooling followed by stirring for 4 hours at the same temperature. The reaction mixture was evaporated and the residue was washed with diethyl ether, dried and then dissolved in water (20 ml). The solution was adjusted to pH 5.9 with 1 N aqueous solution of sodium hydroxide, and filtered to remove insoluble substances. The filtrate was subjected to column chromatography (Non-ion adsorption resin, Diaion HP20 prepared by Mitsubishi Chemical Industries) and the resin was washed with water (70 ml) and then eluted with 20% aqueous solution of isopropyl alcohol. The eluates containing the object compound were collected and then concentrated. The residue was lyophilized to give a mixture of 7-[2-methoxyimino-2-(5-amino-1,2,4-thiadiazol-3-yl)acetamido]-3-(4-methyl-1-piperazinyl)carbonyloxymethyl-3-cephem-4-carboxylic acid (syn isomer) and its sodium salt (0.36 g).

I.R. (Nujol) 3300, 1770, 1680, 1600, 1530, 1470 cm$^{-1}$.

N.M.R. (D$_2$O, δ)

$$\left.\begin{array}{c}2.50\\2.90\end{array}\right\}$$

(3H, s), 3.00–3.43 (4H, m), 3.43–3.93 (6H, m), 4.08 (3H, s), 4.53–5.00 (2H, ABq), 5.20 (1H, d, J=4 Hz), 5.83 (1H, d, J=4 Hz).

The N.M.R. spectrum showed the presence of 20% sodium salt of the object compound.

EXAMPLE 21

The following compounds were obtained according to the similar manners to those in Example 19, 20 and optionally by conversion of the products into their desired salts.

(1) 7-[2-(Propoxyimino-2-(2-formamidothiazol-4-yl)-acetamido-3-(4-methyl-1-piperazinyl)carbonyloxymethyl]-3-cephem-4-carboxylic acid.trifluoroacetate (syn isomer).

I.R. (Nujol) 3300, 1790, 1680, 1550, 1470 cm$^{-1}$.

N.M.R. (DMSO-d$_6$, δ) 0.87 (3H, t, J=8 Hz), 1.33–1.93 (2H, m), 2.75 (3H, s), 2.93–3.33 (4H, m), 3.37–3.80 (6H, m), 4.03 (2H, t, J=8 Hz), 4.67, 5.08 (2H, ABq, J=14 Hz), 5.13 (1H, d, J=4 Hz), 5.57–5.97 (1H, broad), 7.35 (1H, s), 8.50 (1H, s), 9.47–9.73 (1H, broad)

(2) 7-[2-(2-Formamidothiazol-4-yl)acetamido]-3-(4-methyl-1-piperazinyl)carbonyloxymethyl-3-cephem-4-carboxylic acid.trifluoroacetate.

I.R. (Nujol) 1775, 1700, 1665, 1530 cm$^{-1}$.

N.M.R. (DMSO-d$_6$, δ) 2.82 (3H, s), 3.1–3.5 (6H, m), 3.5–3.8 (4H, m), 3.75 (2H, s), 4.74, 5.07 (2H, ABq, J=13 Hz), 5.1 (1H, d, J=5 Hz), 5.73 (1H, d,d, J=5 and 8 Hz), 6.96 (1H, s), 8.46 (1H, s), 8.99 (1H, d, J=8 Hz).

(3) 7-[2-Methoxyimino-2-(2-furyl)acetamido]-3-(4-methyl-1-piperazinyl)carbonyloxymethyl-3-cephem-4-carboxylic acid.trifluoroacetate (syn isomer).

I.R. (Nujol) 3300, 1785, 1710, 1670, 1520 cm$^{-1}$.

N.M.R. (DMSO-d$_6$, δ) 2.78 (3H, s), 3.0–3.3 (6H, m), 3.5–3.8 (4H, m), 3.92 (3H, s), 4.7, 5.1 (2H, ABq, J=14 Hz), 5.19 (1H, d, J=5 Hz), 5.82 (1H, d,d, J=5 and 8 Hz), 6.70 (2H, broad s), 7.85 (1H, s), 9.77 (1H, d, J=8 Hz).

(4) 7-Phenylacetamido-3-[N-{2-(N,N-dimethylamino)-ethyl}carbamoyloxymethyl]-3-cephem-4-carboxylic acid.trifluoroacetate.

I.R. (Nujol) 3300, 1780, 1740–1640 cm$^{-1}$.

N.M.R. (DMSO-d$_6$, δ) 2.8 (6H, s), 3.0–3.73 (4H, m), 3.57 (4H, s), 4.87 (2H, d,d, J=14 and 24 Hz), 5.08 (1H, d, J=5 Hz), 5.7 (1H, d,d, J=5 and 8 Hz), 7.3 (5H, s), 7.13–7.67 (1H, m), 9.08 (1H, d, J=8 Hz)

(5) 7-[2-Methoxyimino-2-(2-aminothiazol-4-yl)-acetamido]-3-(4-methyl-1-piperazinyl)carbonyloxymethyl-3-cephem-4-carboxylic acid.dihydrochloride (syn isomer).

N.M.R. ($D_2O$) 3.00 (3H, s), 4.17 (4H, m), 3.55–3.85 (4H, m), 4.07 (3H, s), 4.67–5.00 (2H, ABq, J=14 Hz), 5.25 (1H, d, J=4 Hz), 5.83 (1H, d, J=4 Hz), 7.10 (1H, s).

(6) 7-[2-Propoxyimino-2-(2-aminothiazol-4-yl)-acetamido]-3-(4-methyl-1-piperazinyl)carbonyloxymethyl-3-cephem-4-carboxylic acid (syn isomer) which contains about 25% sodium salt thereof.

I.R. (Nujol) 3300, 1770, 1680, 1610, 1540, 1470 $cm^{-1}$.

(7) 7-[2(2-Aminothiazol-4-yl)acetamido]-3-(4-methyl-1-piperazinyl)carbonyloxymethyl-3-cephem-4-carboxylic acid.dihydrochloride.

I.R. (Nujol) 3250, 1780, 1710, 1690, 1630, 1545 $cm^{-1}$.

(8) 7-[D-2-(4-Hydroxyphenyl)glycinamido]-3-(4-methyl-1-piperazinyl)carbonyloxymethyl-3-cephem-4-carboxylic acid.ditrifluoroacetate.

I.R. (Nujol) 3350, 3170, 1760, 1670, 1590, 1500 $cm^{-1}$.

(9) 7-[D-2-Phenylglycinamido]-3-(4-methyl-1-piperazinyl)carbonyloxymethyl-3-cephem-4-carboxylic acid.trifluoroacetate.formate.

I.R. (Nujol) 3450, 3250, 1780, 1700, 1600 $cm^{-1}$.

(10) 7-phenylacetamido-3-(4-methyl-1-piperazinyl)-carbonyloxymethyl-3-cephem-4-carboxylic acid.trifluoroacetate.

I.R. (Nujol) 3700–2200, 1780, 1710, 1670, 1540, 1500, 1290, 1260, 1235, 1180 $cm^{-1}$.

N.M.R. (DMSO-$d_6$, δ) 2.8 (3H, s), 3.0–3.35 (4H, broad s), 3.35–3.83 (6H, broad s), 3.75 (2H, s), 4.72, 5.1 (2H, d,d, J=12 Hz), 5.07 (1H, d, J=4 Hz), 5.7 (1H, d,d, J=4 and 8 Hz), 7.3 (5H, s), 9.06 (1H, d, J=8 Hz), 10.3 (2H, broad s).

EXAMPLE 22

To a solution of 7-[2-methoxyimino-2-(2-formamidothiazol-4-yl)acetamido]-3-(4-methyl-1-piperazinyl)carbonyloxymethyl-3-cephem-4-carboxylic acid.trifluoroacetate (syn isomer)(1.0 g) in methanol (20 ml) was added conc.hydrochloric acid (0.62 ml) followed by stirring for 2 hours at ambient temperature. The reaction mixture was evaporated and the residue was pulverized in ethyl acetate, collected by filtration, washed with ethyl acetate and diethyl ether and then dried to give 7-[2-methoxyimino-2-(2-aminothiazol-4-yl)acetamido]-3-(4-methyl-1-piperazinyl)carbonyloxymethyl-3-cephem-4-carboxylic acid.dihydrochloride (syn isomer).

N.M.R. ($D_2O$, δ) 3.00 (3H, s), 4.17 (4H, m), 3.55–3.85 (4H, m), 4.07 (3H, s), 4.67–5.00 (2H, ABq, J=14 Hz), 5.25 (1H, d, J=4 Hz), 5.83 (1H, d, J=4 Hz), 7.10 (1H, s).

The assignments of the C-2 protons could not be shown due to the overlap of those of $D_2O$.

EXAMPLE 23

To a mixture of 7-[2-propoxyimino-2-(2-formamidothiazol-4-yl)acetamido]-3-(4-methyl-1-piperazinyl)carbonyloxymethyl-3-cephem-4-carboxylic acid.trifluoroacetate (syn isomer)(1.0 g) in methanol (30 ml) was added conc.hydrochloric acid (0.35 ml) under ice-water cooling and the stirring was continued at the same temperature for 1 hour and 15 minutes and at ambient temperature for 3 hours. The reaction mixture was treated with activated charcoal and evaporated under reduced pressure. The residue was pulverized in ethyl acetate, collected by filtration, washed with ethyl acetate and then dissolved in water (40 ml). The solution was adjusted to pH 6.0 with 1 N aqueous solution of sodium hydroxide and filtered to remove insoluble substances. The filtrate was subjected to column chromatography (Non-ion adsorption resin, Diaion HP 20 prepared by Mitsubishi Chemical Industries)(40 ml) and the resin was washed with water (80 ml) and then eluted with 20% isopropyl alcohol. The eluates containing the object compound were collected and then concentrated. The residue was lyophilized to give a mixture of 7-[2-propoxyimino-2-(2-aminothiazol-4-yl)acetamido]-3-(4-methyl-1-piperazinyl)carbonyloxymethyl-3-cephem-4-carboxylic acid (syn isomer) and its sodium salt (360 mg).

I.R. (Nujol) 3300, 1770, 1680, 1610, 1540, 1470 $cm^{-1}$.

N.M.R. ($D_2O$, δ) 0.88 (3H, t, J=8 Hz), 1.66 (2 H, q, J=8 Hz), $$\left.\begin{array}{c}2.50\\2.84\end{array}\right\}$$

(3H, s), 3.00–3.36 (4H, m), 3.40–3.92 (6H, m), 4.12 (2H, t, J=8 Hz), 4.40–5.13 (2H, ABq), 5.16 (1H, d, J=4 Hz), 5.78 (1H, d, J=4 Hz), 6.92 (1H, s).

The N.M.R. data showed the presence of 25% sodium salt of the object compound.

EXAMPLE 24

A mixture of 7-[2-(2-formamidothiazol-4-yl)acetamido]-3-(4-methyl-1-piperazinyl)carbonyloxymethyl-3-cephem-4-carboxylic acid.trifluoroacetate (1.25 g) and conc.hydrochloric acid (0.6 ml) in methanol (12 ml) and tetrahydrofuran (12 ml) was stirred for 1 hour and 15 minutes at ambient temperature. The reaction mixture was treated with activated charcoal and filtered. The filtrate was evaporated and to the residue was added isopropyl alcohol followed by evaporation. The residue was pulverized in diethyl ether, collected by filtration, washed with ethyl acetate and then dried under reduced pressure to give 7-[2-(2-aminothiazol-4-yl)acetamido]-3-(4-methyl-1-piperazinyl)carbonyloxymethyl-3-cephem-4-carboxylic acid.dihydrochloride (0.65 g).

I.R. (Nujol) 3250, 1780, 1710, 1690, 1630, 1545 $cm^{-1}$.

N.M.R. (DMSO-$d_6$, δ) 2.77 (3H, s), 3.1–4.0 (8H, m), 3.48 (2H, s), 3.67 (2H, broad s), 4.72, 5.14 (2H, Abq, J=14 Hz), 5.13 (1H, d, J=5 Hz), 5.74 (1H, d,d, J=5 and 8 Hz), 6.70 (1H, s), 9.22 (1H, d, J=8 Hz).

EXAMPLE 25

A mixture of benzhydryl 7-[D-N-tert-butoxycarbonyl-2-(4-hydroxyphenyl)glycinamido]-3-(4-methyl-1-piperazinyl)carbonyloxymethyl-3-cephem-4-carboxylate.trifluoroacetate (1.85 g) and formic acid (6 ml) was stirred for 3 hours and 20 minutes at ambient temperature. The reaction mixture was evaporated and the residue was pulverized with ethyl acetate, collected by filtration. Thus obtained powder was washed with ethyl acetate, acetone (20 ml), ethanol (20 ml) and 80% ethanol (20 ml) in turn and then dried to give 7-[D-2-(4-hydroxyphenyl)glycinamido]-3-(4-methyl-1-piperazinyl)carbonyloxymethyl-3-cephem-4-carboxylic acid.ditrifluoroacetate (0.55 g). Further, the washings were combined and evaporated and then the residue was pulverized in a mixture of ethanol and acetone to give the same object compound (0.4 g).

I.R. (Nujol) 3350, 3170, 1760, 1670, 1590, 1500 cm$^{-1}$.

N.M.R. (DMSO-$d_6$, δ) 2.8 (3H, s), 3–3.3 (4H, m), 3.4–3.8 (6H, m), 4.9–5.3 (4H, m), 5.7 (1H, d, J=5 Hz), 6.88, 7.38 (4H, ABq, J=8 Hz).

EXAMPLE 26

A mixture of benzhydryl 7-(D-N-tert-butoxycarbonyl-2-phenylglycinamido)-3-(4-methyl-1-piperazinyl)-carbonyloxymethyl-3-cephem-4-caboxylate. trifluoroacetate (1.75 g) and formic acid (6 ml) in methylene chloride (2 ml) was stirred for 6 hours and 10 minutes. The reaction mixture was evaporated and the residue was washed with diethyl ether, ethyl acetate and acetone and then dried to give 7-(D-2-phenylglycinamido)-3-(4-methyl-1-piperazinyl)carbonyloxymethyl-3-cephem-4-carboxylic acid.trifluoroacetate.formate (1.2 g).

I.R. (Nujol) 3450, 3250, 1780, 1700; 1600 cm$^{-1}$.

N.M.R. (DMSO-$d_6$=$D_2O$, δ) 2.66 (3H, s), 2.8–3.2 (4H, m), 3.3–3.7 (6H, m), 4.67, 5,27 (2H, ABq, J=12 Hz), 4.97 (1H, d, J=5 Hz), 5.06 (1H, s), 5.69 (1H, d, J=5 Hz), 7.4 (5H, s), 8.20 (1H, s).

EXAMPLE 27

The following compound was obtained according to the similar manners to those in Examples 22–26.

(1) 7-[2-Methoxyimino-2-(5-amino-1,2,4-thiadiazol-3-yl)acetamido]-3-(4-methyl-1-piperazinyl)carbonyloxymethyl-3-cephem-4-carboxylic acid (syn isomer) which contains about 20% sodium salt thereof.

I.R. (Nujol) 3300, 1770, 1680, 1600, 1530, 1470 cm$^{-1}$.

What we claim is:

1. 3,7-Disubstituted-2 or 3-cephem-4-carboxylic acid compounds of the formula:

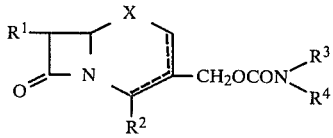

wherein $R^1$ is acylamino or ar(lower)alkylamino; $R^2$ is carboxy or carboxy protected by a pharmaceutically acceptable group; —N—$R^3$, $R^4$ is di(lower)alkylamino(lower)alkylamino, an unsaturated or saturated 3 to 8 membered heteromonocyclic (lower)alkylamino group containing 1 to 4 nitrogen atoms, an unsaturated or saturated 3 to 8 membered heteromonocyclic (lower)alkylamino group containing 1 to 4 nitrogen atoms substituted by lower alkyl or hydroxy(lower) alkyl, an unsaturated or saturated 5 to 6 membered heteromonocyclic group containing 2 to 4 nitrogen atoms, an unsaturated or saturated 5 to 6 membered heteromonocyclic group containing 2 to 4 nitrogen atoms substituted by lower alkyl or hydroxy(lower)alkyl or hydroxypiperidino, and X is —S— or

and pharmaceutically acceptable salts thereof.

2. The compound of claim 1, wherein
$R^1$ is acylamino;
$R^2$ is carboxy or an esterified carboxy group; and the group of the formula:

is di(lower)alkylamino(lower)alkylamino, lower alkylpyrrolidinyl(lower)alkylamino, lower alkylpiperazinyl, hydroxy(lower)alkylpiperazinyl, imidazolyl or hydroxypiperidino.

3. The compound of claim 2 wherein
$R^1$ is, lower alkoxycarbonylamino which may have 1 to 3 halogen atom(s), phenyl(lower)alkanoylamino which may have hydroxy and/or amino and/or lower alkoxycarbonylamino, thiazolyl(lower)alkanoylamino which may have lower alkoxyimino and/or amino and/or lower alkanoylamino, thiadiazolyl(lower)alkanoylamino having lower alkoxyimino and/or amino and/or lower alkanoylamino, or furyl(lower)alkanoylamino having lower alkoxyimino; and
$R^2$ is carboxy or mono(or di or tri)phenyl(lower)alkoxycarbonyl.

4. The compound of claim 3, wherein
$R^1$ is 2-lower alkoxyimino-2-(aminothiazolyl-)acetamido;
$R^2$ is carboxy;
the group of the formula:

is lower alkylpiperazinyl; and
X is —S—.

5. The compound of claim 4, which is 7-[2-methoxyimino-2-(2-aminothiazol-4-yl)acetamido]-3-(4-methyl-1-piperazinyl)carbonyloxymethyl-3-cephem-4-carboxylic acid (syn isomer) or its hydrochloride.

6. The compound of claim 4, which is 7-[2-propoxyimino-2-(2-aminothiazol-4-yl)acetamido]-3-(4-methyl-1-piperazinyl)carbonyloxymethyl-3-cephem-4-carboxylic acid (syn isomer) or its sodium salt.

7. The compound of claim 3, wherein
$R^1$ is 2-lower alkoxyimino-2-(aminothiadiazolyl-)acetamido;
$R^2$ is carboxy;
the group of the formula:

is lower alkylpiperazinyl; and
X is —S—.

8. The compound of claim 7 which is 7-[2-methoxyimino-2-(5-amino-1,2,4-thiadiazol-3-yl)acetamido]-3-(4-methyl-1-piperazinyl)carbonyloxymethyl-3-cephem-4-carboxylic acid (syn isomer) or its sodium salt.

9. A pharmaceutical composition effective for the treatment of infectious diseases in mammals, comprising a therapeutically effective amount of the compound of claim 1 or pharmaceutically acceptable salt thereof in association with a pharmaceutically acceptable, substantially nontoxic carrier or excipient.

* * * * *